United States Patent [19]
Tay et al.

[11] Patent Number: 5,810,810
[45] Date of Patent: Sep. 22, 1998

[54] APPARATUS AND METHOD FOR SEALING VASCULAR PUNCTURES

[75] Inventors: Sew-Wah Tay, Plymouth; Kemal Schankereli, Stillwater; Hans Mische, St. Cloud; Thomas Holman, Minneapolis, all of Minn.

[73] Assignee: Scimed Life Systems, Inc., Maple Grove, Minn.

[21] Appl. No.: 472,717

[22] Filed: Jun. 6, 1995

Related U.S. Application Data

[63] Continuation-in-part of Ser. No. 55,634, Apr. 30, 1993, which is a continuation-in-part of Ser. No. 873,955, Apr. 23, 1992, abandoned.

[51] Int. Cl.$^6$ .................................................. A61B 17/36
[52] U.S. Cl. ............................................................. 606/50
[58] Field of Search ...................................... 128/642, 898, 128/662.05, 662.06; 606/34, 37, 40, 41, 49, 50

[56] References Cited

U.S. PATENT DOCUMENTS

| | | |
|---|---|---|
| Re. 33,925 | 5/1992 | Bales et al. . |
| 1,596,004 | 8/1926 | De Bengoa . |
| 1,731,069 | 10/1929 | Herman . |
| 1,983,669 | 12/1934 | Kimble . |
| 2,790,442 | 4/1957 | Donaldson . |
| 2,808,833 | 10/1957 | August . |
| 3,100,489 | 8/1963 | Bagley . |
| 3,176,114 | 3/1965 | Kneisley . |
| 3,301,258 | 1/1967 | Werner et al. . |
| 3,302,635 | 2/1967 | Pittman . |
| 3,494,364 | 2/1970 | Peters . |
| 3,532,095 | 10/1970 | Miller . |
| 3,613,682 | 10/1971 | Naylor . |
| 3,636,943 | 1/1972 | Balamuth . |
| 3,699,967 | 10/1972 | Anderson . |
| 3,794,040 | 2/1974 | Balamuth . |
| 3,801,766 | 4/1974 | Morrison, Jr. . |
| 3,801,800 | 4/1974 | Newton . |
| 3,825,004 | 7/1974 | Durden, III . |
| 3,858,586 | 1/1975 | Lessen . |

(List continued on next page.)

FOREIGN PATENT DOCUMENTS

| | | |
|---|---|---|
| 0 075 860 A2 | 4/1983 | European Pat. Off. . |
| 0 476 178 A1 | 3/1992 | European Pat. Off. . |
| 0 482 350 A2 | 4/1992 | European Pat. Off. . |
| 0 521 595 A2 | 1/1993 | European Pat. Off. . |
| 38 38840 A1 | 5/1990 | Germany . |
| WO 90/14796 | 12/1990 | WIPO . |
| WO 92/05740 | 4/1992 | WIPO . |
| WO 92/22252 | 12/1992 | WIPO . |
| WO 93/21844 | 11/1993 | WIPO . |
| WO 94/24948 | 11/1994 | WIPO . |

OTHER PUBLICATIONS

Article entitled "The Mechanism of Blood Vessel Closure By High Frequency Electrocoagulation" by Bernard Sigel and Marvin R. Dunn, *Surgery Gynecology & Obstetrics*, Oct. 1965, vol. 121, No. 4, pp. 823–831.

Article entitled "Repair of small blood vesses with the Neodymium–YAG laser: A preliminary report" by K.K. Jain and W. Gorisch, *Surgery*, vol. 85, No. 6, pp. 684–688.

*Primary Examiner*—John P. Lacyk
*Assistant Examiner*—Samuel Gilbert
*Attorney, Agent, or Firm*—Brinks Hofer Gilson & Lione; Steven P. Shurtz

[57] ABSTRACT

An apparatus for closing and sealing a vascular puncture is connected to an energy supply such that heat is generated in, or thermally conducted to, the tissue, thereby thermally fusing the vascular tissue together. The method for closing and sealing a vascular puncture comprises applying radio frequency or other energy to the tissue, the energy being sufficient to thermally fuse the tissue together, thus sealing the puncture. Embodiments of depth finding and guiding devices, as well as blood vessel occluders, are also disclosed.

12 Claims, 20 Drawing Sheets

U.S. PATENT DOCUMENTS

| | | |
|---|---|---|
| 3,874,388 | 4/1975 | King et al. . |
| 3,886,944 | 6/1975 | Jamshidi . |
| 3,920,021 | 11/1975 | Hiltebrandt . |
| 3,929,137 | 12/1975 | Gonser . |
| 3,938,527 | 2/1976 | Rioux et al. . |
| 3,963,030 | 6/1976 | Newton . |
| 3,978,863 | 9/1976 | Fettel et al. . |
| 3,980,085 | 9/1976 | Ikuno . |
| 4,003,380 | 1/1977 | Wien . |
| 4,007,743 | 2/1977 | Blake . |
| 4,011,872 | 3/1977 | Komiya . |
| 4,014,343 | 3/1977 | Esty . |
| 4,016,881 | 4/1977 | Rioux et al. . |
| 4,043,342 | 8/1977 | Morrison, Jr. . |
| 4,051,855 | 10/1977 | Schneiderman . |
| 4,054,143 | 10/1977 | Bauer . |
| 4,074,718 | 2/1978 | Morrison, Jr. . |
| 4,112,950 | 9/1978 | Pike . |
| 4,122,853 | 10/1978 | Smith . |
| 4,162,673 | 7/1979 | Patel . |
| 4,168,708 | 9/1979 | Lepley, Jr. et al. . |
| 4,198,957 | 4/1980 | Cage et al. . |
| 4,215,699 | 8/1980 | Patel . |
| 4,228,800 | 10/1980 | Degler, Jr. et al. . |
| 4,230,119 | 10/1980 | Blum . |
| 4,269,174 | 5/1981 | Adair . |
| 4,271,847 | 6/1981 | Stokes . |
| 4,273,127 | 6/1981 | Auth et al. . |
| 4,314,555 | 2/1982 | Sagae . |
| 4,353,371 | 10/1982 | Cosman . |
| 4,359,052 | 11/1982 | Staub . |
| 4,370,980 | 2/1983 | Lottick . |
| 4,390,018 | 6/1983 | Zukowski . |
| 4,404,971 | 9/1983 | LeVeen et al. . |
| 4,411,266 | 10/1983 | Cosman . |
| 4,418,692 | 12/1983 | Guay . |
| 4,424,833 | 1/1984 | Spector et al. . |
| 4,470,415 | 9/1984 | Wozniak . |
| 4,476,862 | 10/1984 | Pao . |
| 4,483,338 | 11/1984 | Bloom et al. . |
| 4,492,231 | 1/1985 | Auth . |
| 4,498,475 | 2/1985 | Schneiderman . |
| 4,520,823 | 6/1985 | LeVeen et al. . |
| 4,522,205 | 6/1985 | Taylor et al. . |
| 4,532,924 | 8/1985 | Auth et al. . |
| 4,539,987 | 9/1985 | Nath et al. . |
| 4,548,207 | 10/1985 | Reimels . |
| 4,625,724 | 12/1986 | Suzuki et al. . |
| 4,637,392 | 1/1987 | Sorochenko . |
| 4,645,491 | 2/1987 | Evans . |
| 4,671,274 | 6/1987 | Sorochenko . |
| 4,672,969 | 6/1987 | Dew . |
| 4,682,596 | 7/1987 | Bales et al. . |
| 4,708,136 | 11/1987 | Saito . |
| 4,716,897 | 1/1988 | Noguchi et al. . |
| 4,717,381 | 1/1988 | Papantonakos . |
| 4,735,201 | 4/1988 | O'Reilly . |
| 4,744,359 | 5/1988 | Hatta et al. . |
| 4,744,364 | 5/1988 | Kensey . |
| 4,760,847 | 8/1988 | Vaillancourt . |
| 4,765,331 | 8/1988 | Petruzzi et al. . |
| 4,776,349 | 10/1988 | Nashef et al. . |
| 4,790,819 | 12/1988 | Li et al. . |
| 4,801,293 | 1/1989 | Jackson . |
| 4,832,688 | 5/1989 | Sagae et al. . |
| 4,834,725 | 5/1989 | Iwatschenko . |
| 4,836,204 | 6/1989 | Landymore et al. . |
| 4,848,339 | 7/1989 | Rink et al. . |
| 4,848,352 | 7/1989 | Pohndorf et al. ............ 128/642 |
| 4,850,960 | 7/1989 | Grayzel . |
| 4,852,568 | 8/1989 | Kensey . |
| 4,854,320 | 8/1989 | Dew et al. . |
| 4,860,745 | 8/1989 | Farin et al. . |
| 4,890,612 | 1/1990 | Kensey . |
| 4,900,303 | 2/1990 | Lemelson . |
| 4,917,089 | 4/1990 | Sideris . |
| 4,920,980 | 5/1990 | Jackowski ..................... 128/642 X |
| 4,921,478 | 5/1990 | Solano et al. . |
| 4,929,246 | 5/1990 | Sinofsky . |
| 4,938,761 | 7/1990 | Ensslin . |
| 4,943,290 | 7/1990 | Rexroth et al. . |
| 4,946,463 | 8/1990 | Wright . |
| 4,953,559 | 9/1990 | Salerno . |
| 4,960,133 | 10/1990 | Hewson . |
| 4,961,729 | 10/1990 | Vaillancourt . |
| 4,979,948 | 12/1990 | Geddes et al. . |
| 4,994,060 | 2/1991 | Rink et al. . |
| 5,002,051 | 3/1991 | Dew et al. . |
| 5,009,656 | 4/1991 | Reimels . |
| 5,013,312 | 5/1991 | Parins et al. . |
| 5,021,059 | 6/1991 | Kensey et al. . |
| 5,035,695 | 7/1991 | Weber, Jr. et al. . |
| 5,038,789 | 8/1991 | Frazin ........................ 128/662.06 |
| 5,047,028 | 9/1991 | Qian . |
| 5,049,148 | 9/1991 | Mehl . |
| 5,053,046 | 10/1991 | Janese . |
| 5,057,105 | 10/1991 | Malone et al. . |
| 5,061,267 | 10/1991 | Zeiher . |
| 5,061,274 | 10/1991 | Kensey . |
| 5,073,166 | 12/1991 | Parks et al. . |
| 5,078,743 | 1/1992 | Mikalov et al. . |
| 5,080,660 | 1/1992 | Buelna . |
| 5,085,659 | 2/1992 | Rydell . |
| 5,088,997 | 2/1992 | Delahuerga et al. . |
| 5,108,392 | 4/1992 | Spingler . |
| 5,108,420 | 4/1992 | Marks . |
| 5,108,421 | 4/1992 | Fowler . |
| 5,116,332 | 5/1992 | Lottick . |
| 5,122,137 | 6/1992 | Lennox . |
| 5,122,139 | 6/1992 | Sutter . |
| 5,129,882 | 7/1992 | Weldon et al. . |
| 5,131,394 | 7/1992 | Gehlbach . |
| 5,133,714 | 7/1992 | Beane . |
| 5,141,515 | 8/1992 | Eberbach . |
| 5,147,316 | 9/1992 | Castillenti . |
| 5,147,357 | 9/1992 | Rose et al. . |
| 5,151,098 | 9/1992 | Loertscher . |
| 5,151,102 | 9/1992 | Kamiyama et al. . |
| 5,156,613 | 10/1992 | Sawyer . |
| 5,158,561 | 10/1992 | Rydell et al. . |
| 5,159,925 | 11/1992 | Neuwirth et al. . |
| 5,183,464 | 2/1993 | Dubrul et al. . |
| 5,188,634 | 2/1993 | Hussein et al. . |
| 5,190,541 | 3/1993 | Abele et al. . |
| 5,192,300 | 3/1993 | Fowler . |
| 5,192,302 | 3/1993 | Kensey et al. . |
| 5,207,675 | 5/1993 | Canady . |
| 5,217,024 | 6/1993 | Dorsey et al. . |
| 5,217,451 | 6/1993 | Freitas . |
| 5,217,458 | 6/1993 | Parins . |
| 5,217,459 | 6/1993 | Kamerling . |
| 5,217,460 | 6/1993 | Knoepfler . |
| 5,220,924 | 6/1993 | Frazin ........................ 128/662.06 |
| 5,221,259 | 6/1993 | Weldon et al. . |
| 5,221,281 | 6/1993 | Klicek et al. . |
| 5,222,974 | 6/1993 | Kensey et al. . |
| 5,226,908 | 7/1993 | Yoon . |
| 5,230,349 | 7/1993 | Langberg . |
| 5,257,635 | 11/1993 | Langberg . |
| 5,258,006 | 11/1993 | Rydell et al. . |
| 5,269,780 | 12/1993 | Roos . |
| 5,275,616 | 1/1994 | Fowler . |

| | | | | | | |
|---|---|---|---|---|---|---|
| 5,277,696 | 1/1994 | Hagen | 606/50 | 5,370,660 | 12/1994 | Weinstein et al. . |
| 5,281,216 | 1/1994 | Klicek . | | 5,383,896 | 1/1995 | Gershony et al. . |
| 5,282,799 | 2/1994 | Rydell . | | 5,383,899 | 1/1995 | Hammerslag . |
| 5,282,827 | 2/1994 | Kensey et al. . | | 5,411,520 | 5/1995 | Nash et al. . |
| 5,290,310 | 3/1994 | Makower et al. . | | 5,413,571 | 5/1995 | Katsaros et al. . |
| 5,292,332 | 3/1994 | Lee . | | 5,415,657 | 5/1995 | Taymor-Luria . |
| 5,304,117 | 4/1994 | Wilk . | | 5,419,765 | 5/1995 | Weldon et al. . |
| 5,306,254 | 4/1994 | Nash et al. . | | 5,431,639 | 7/1995 | Shaw . |
| 5,320,639 | 6/1994 | Rudnick . | | 5,437,631 | 8/1995 | Janzen . |
| 5,324,306 | 6/1994 | Makower et al. . | | 5,441,517 | 8/1995 | Kensey et al. . |
| 5,364,389 | 11/1994 | Anderson . | | 5,507,744 | 4/1996 | Tay et al. . |

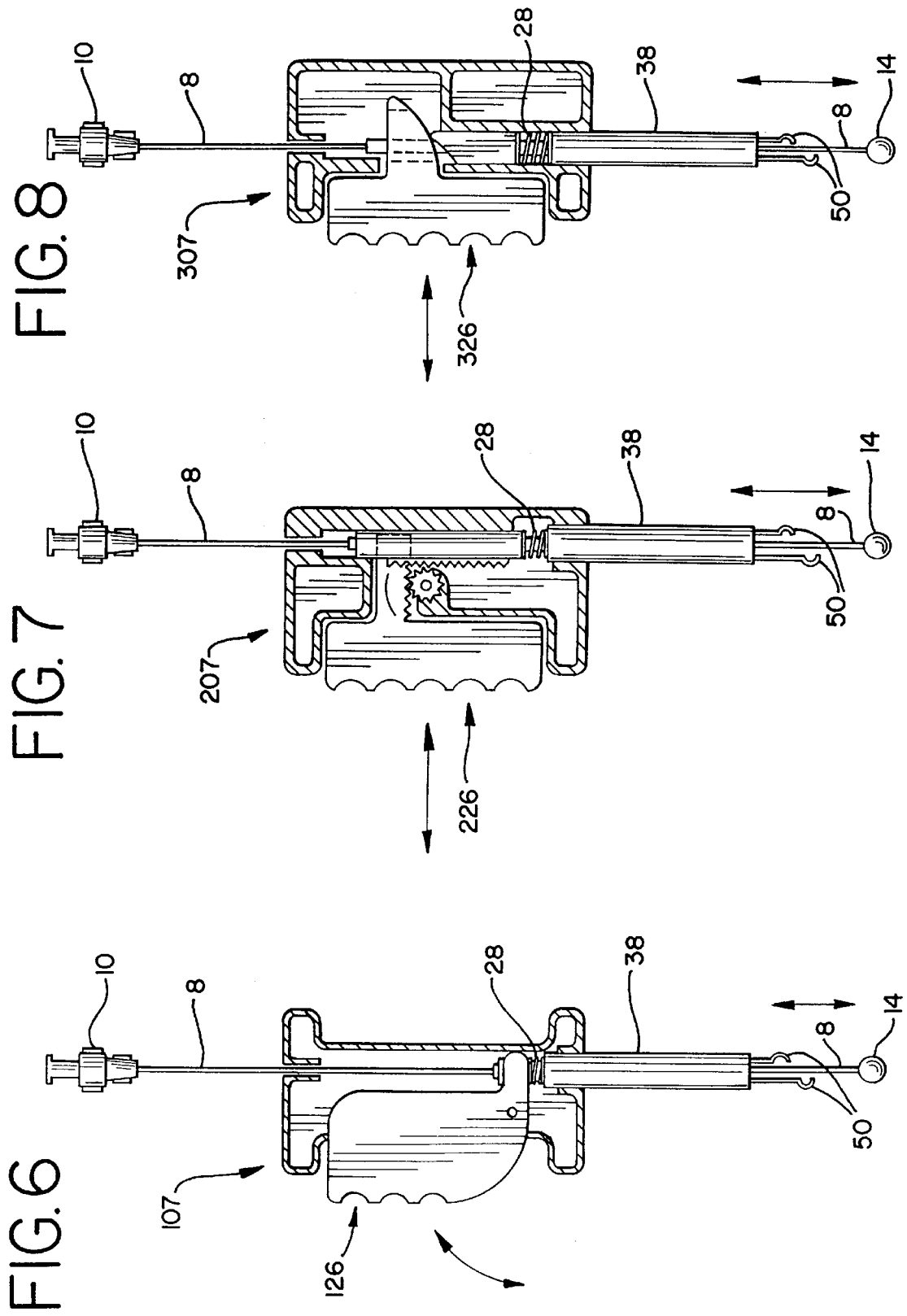

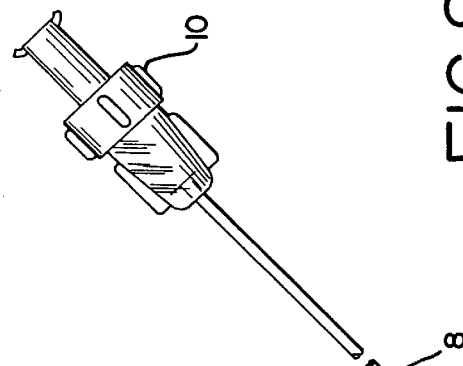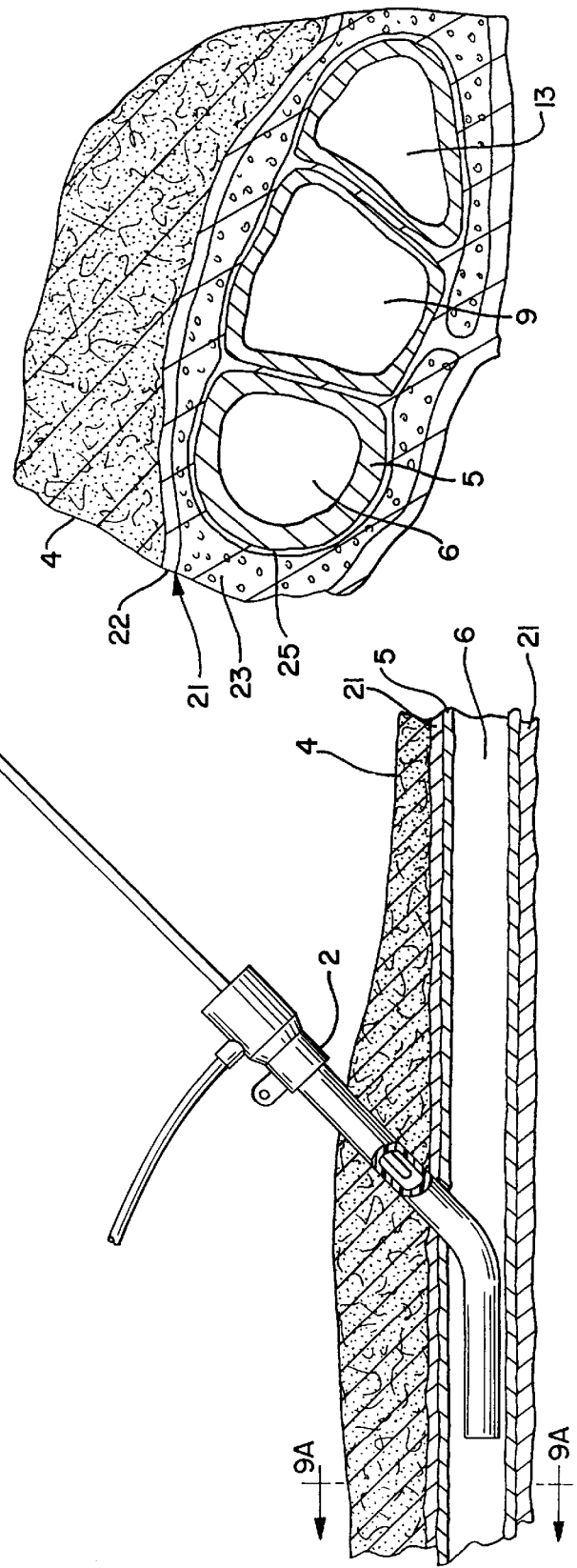

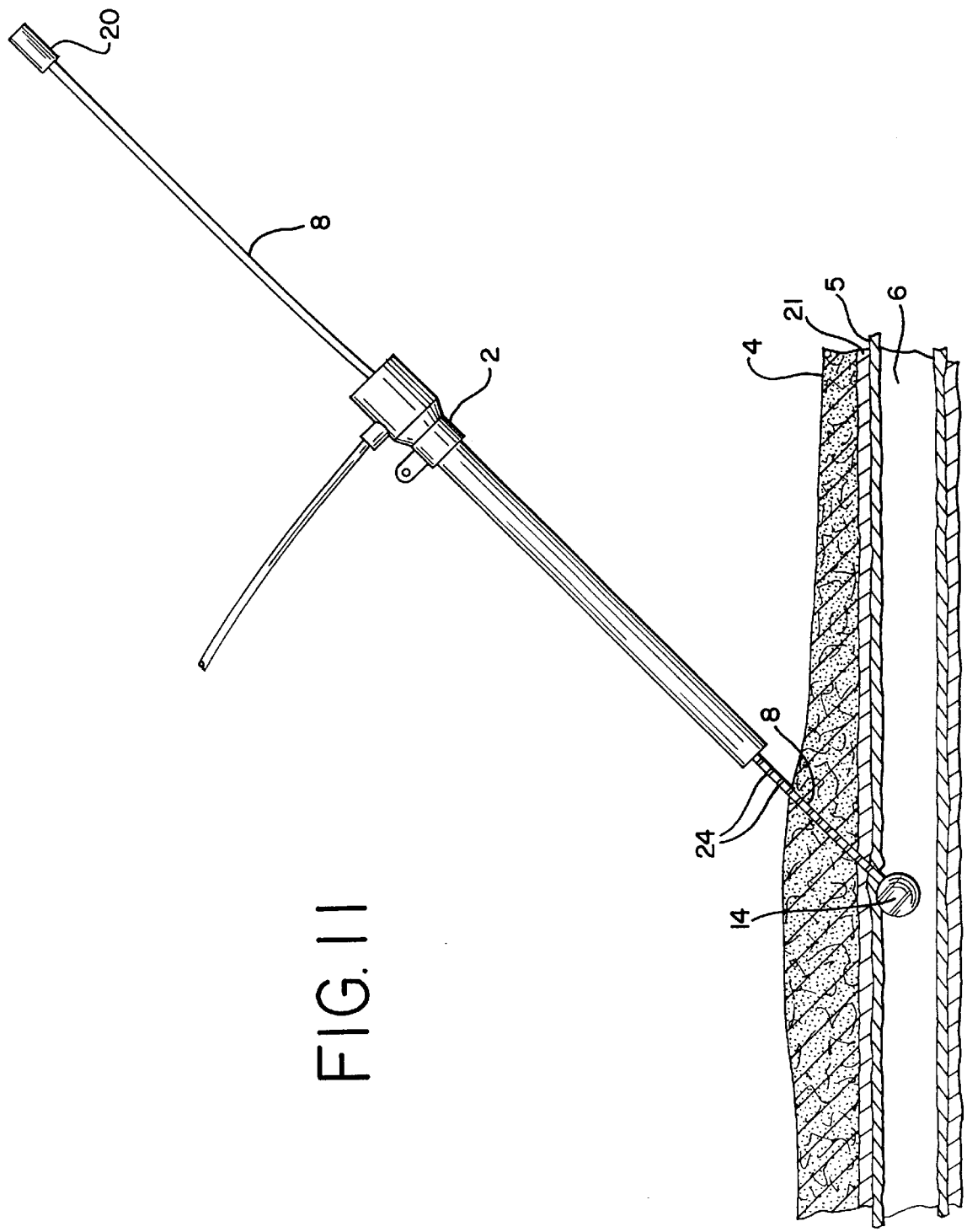

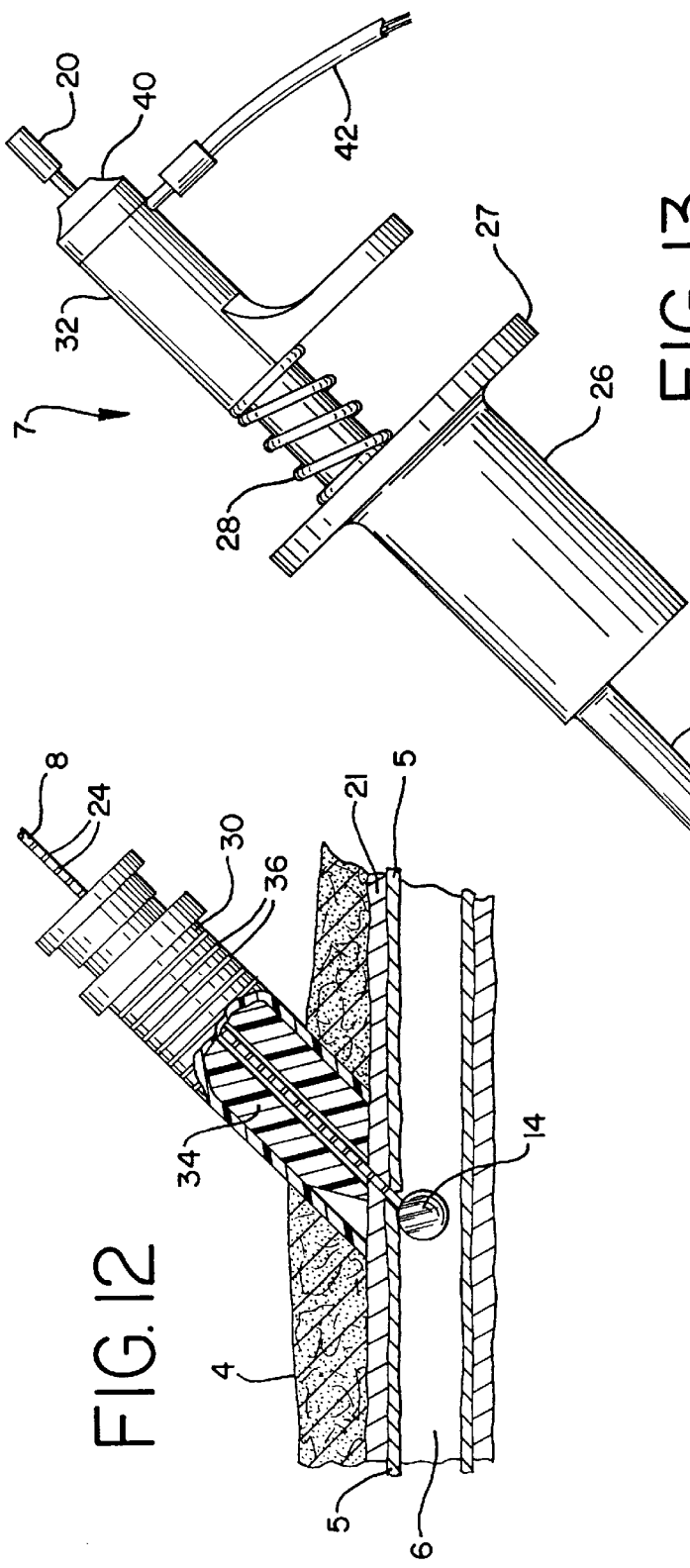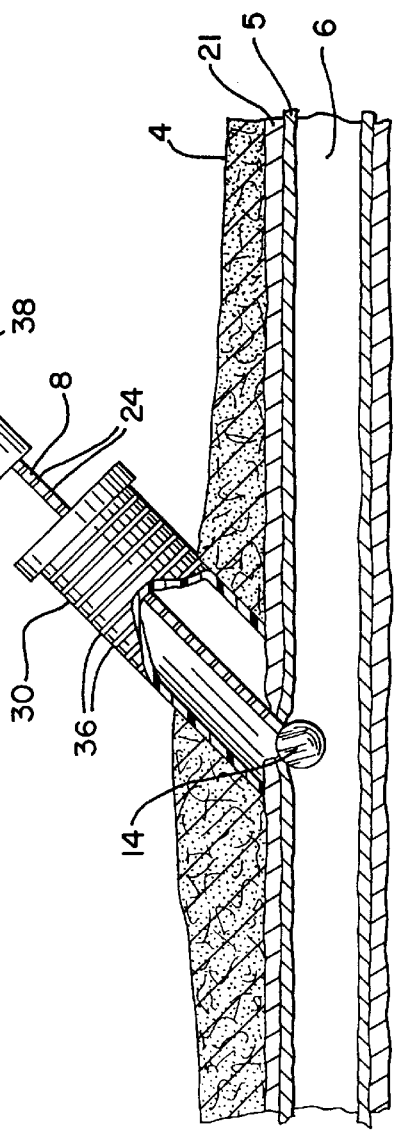

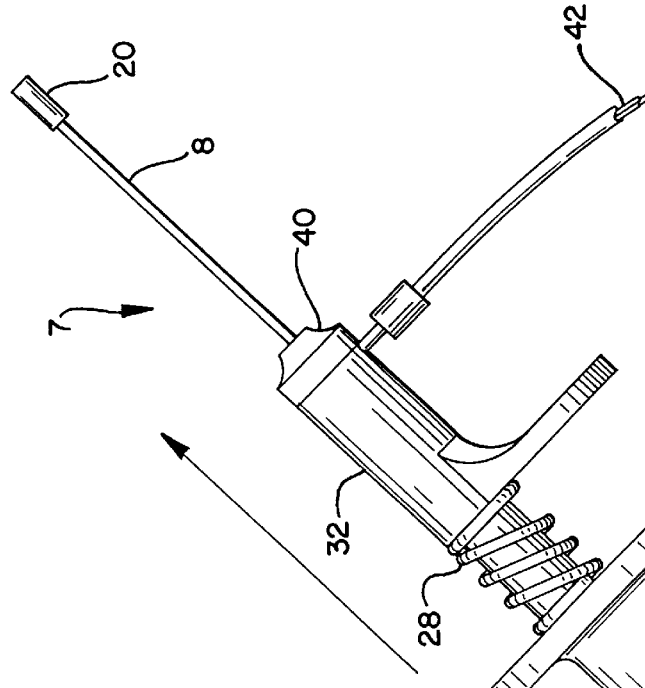
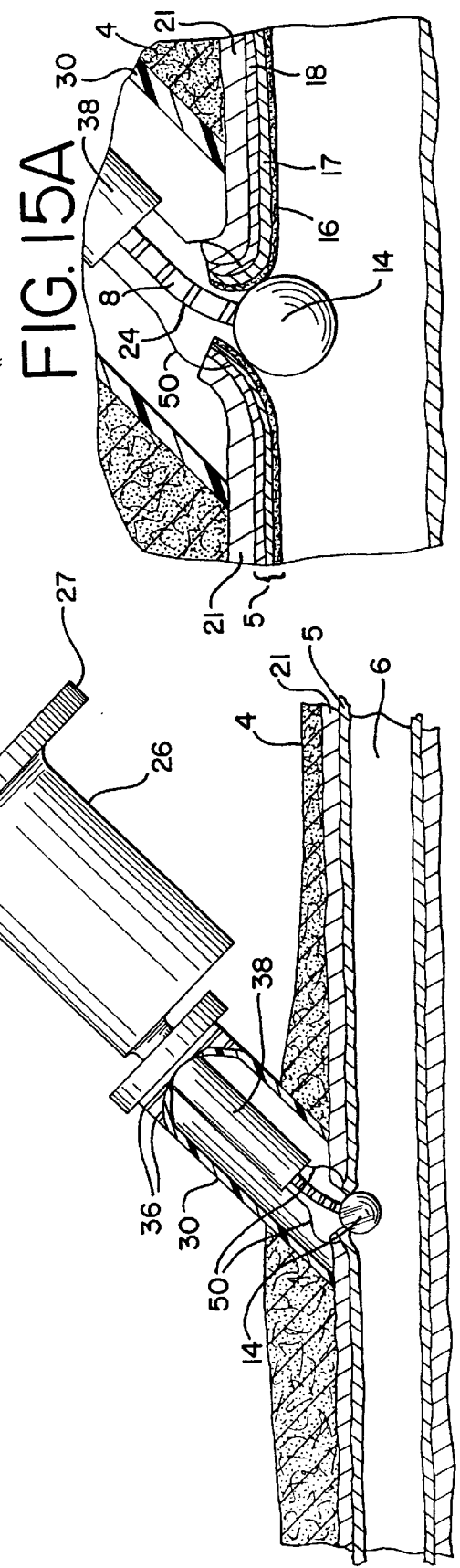

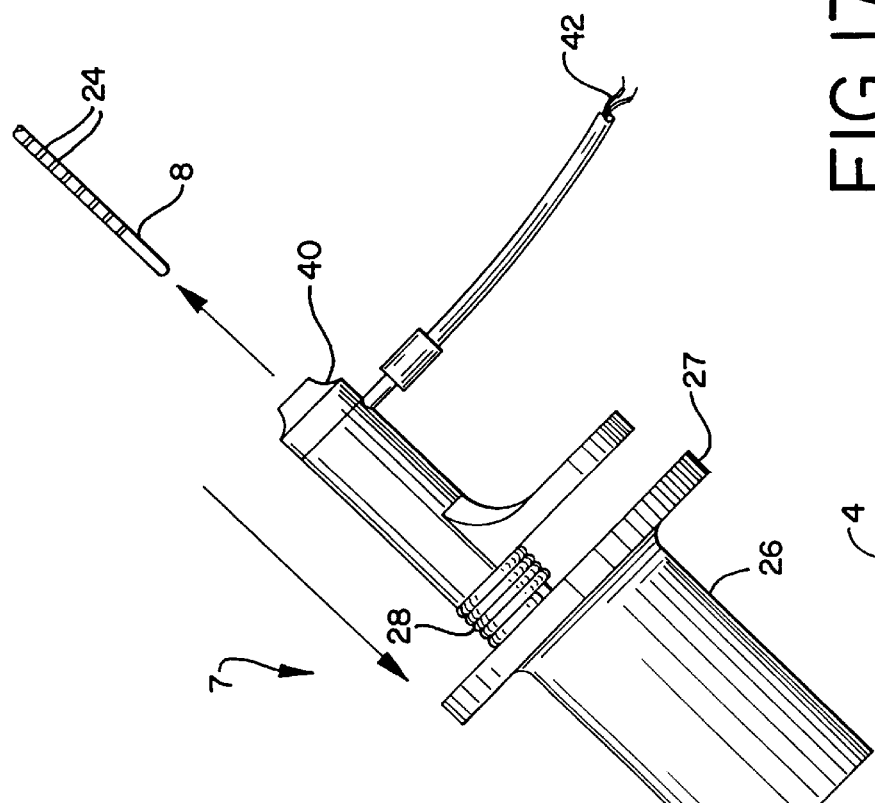
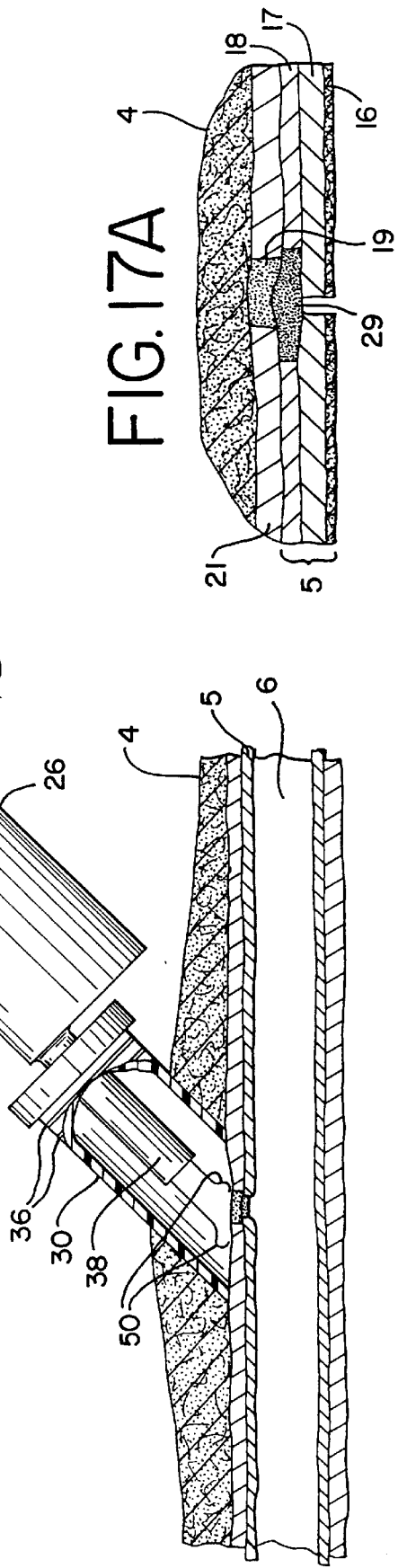

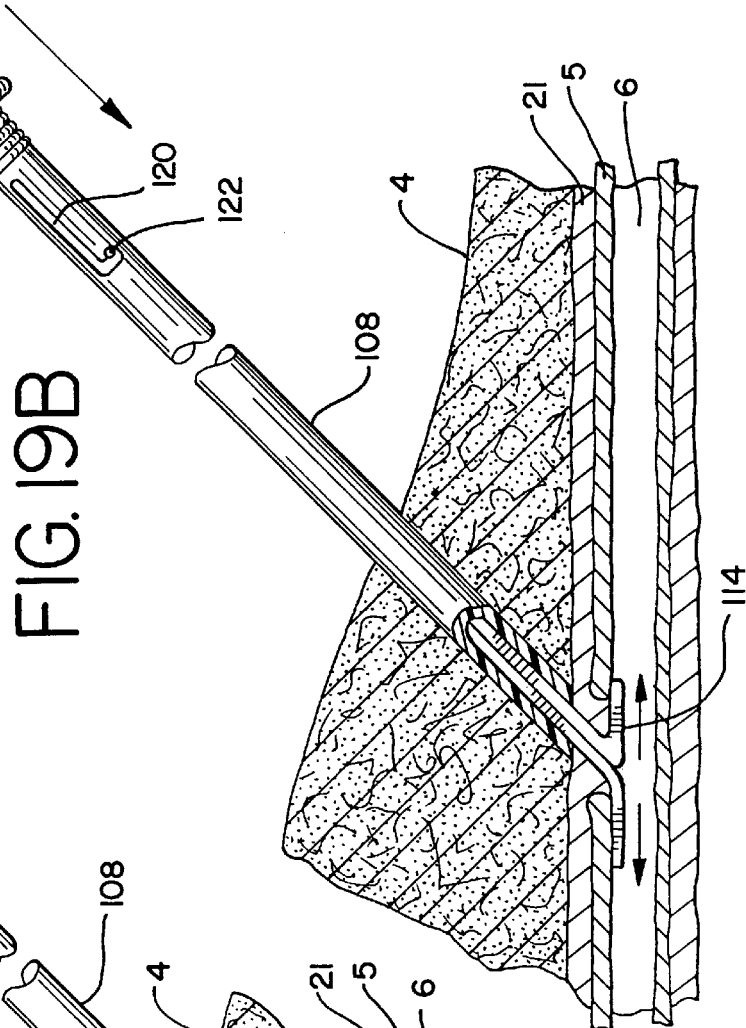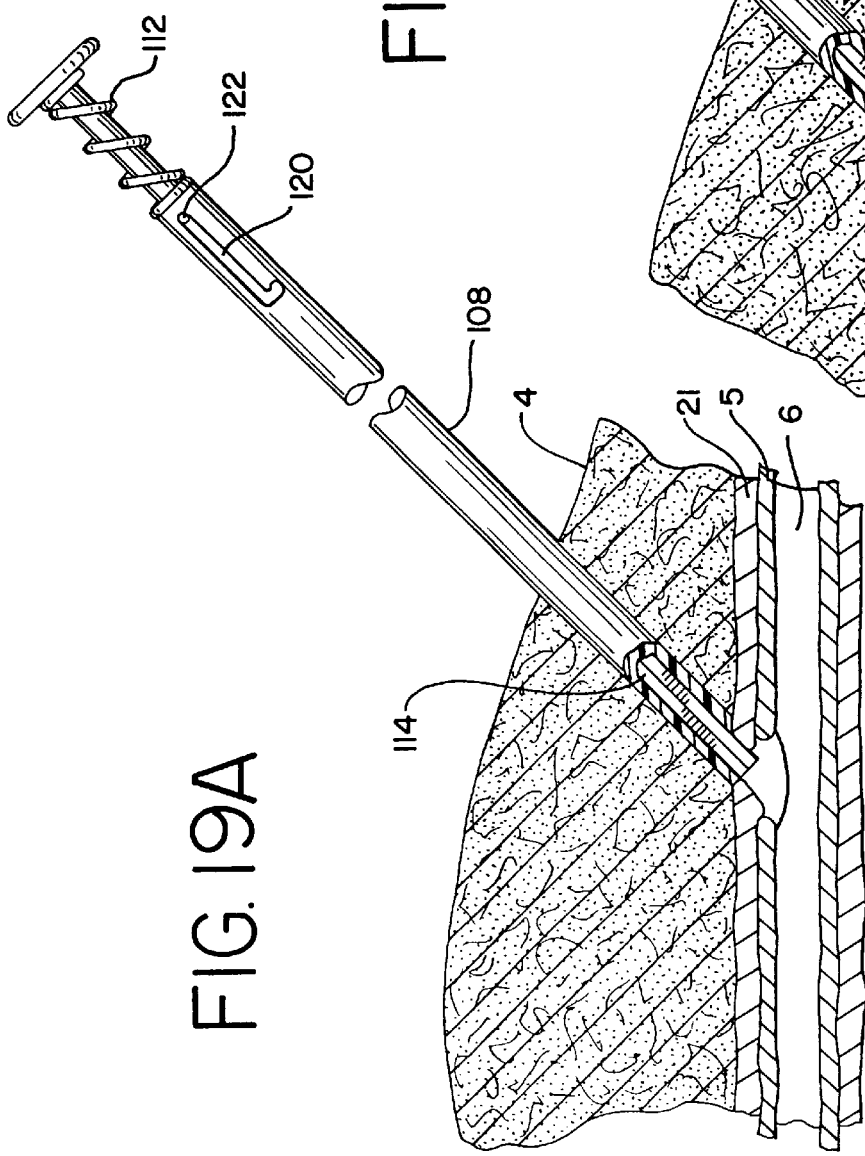

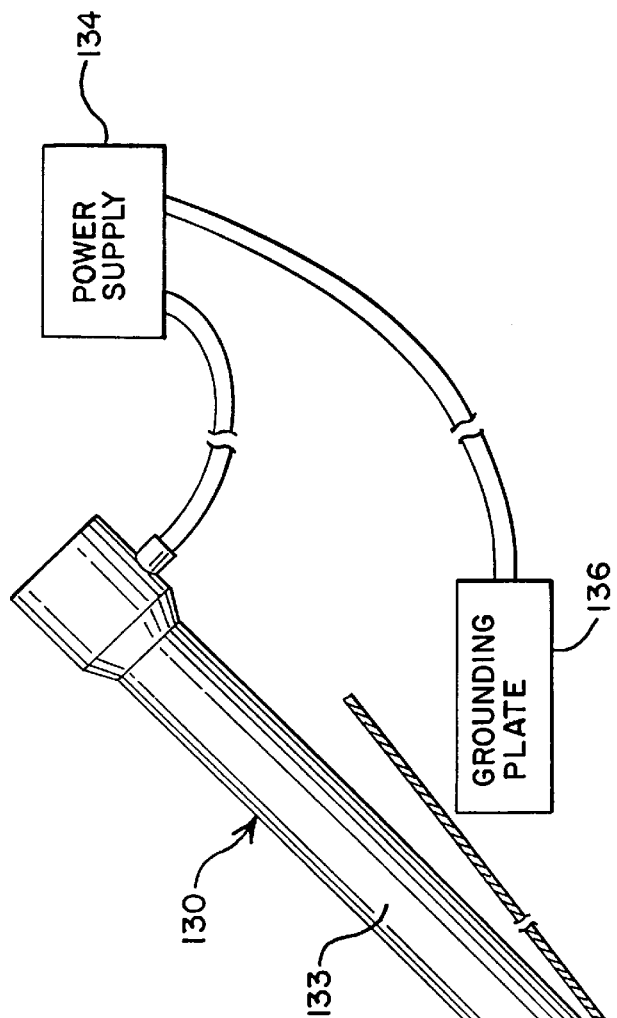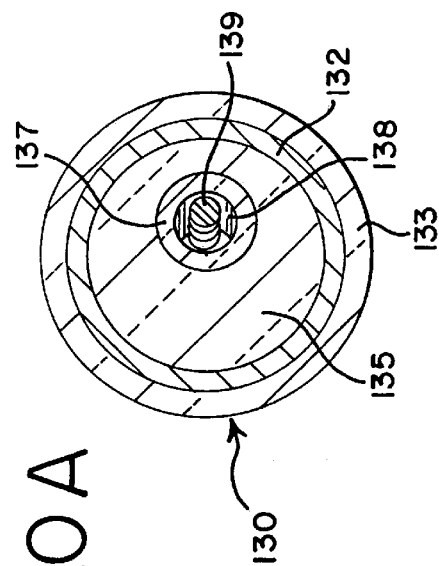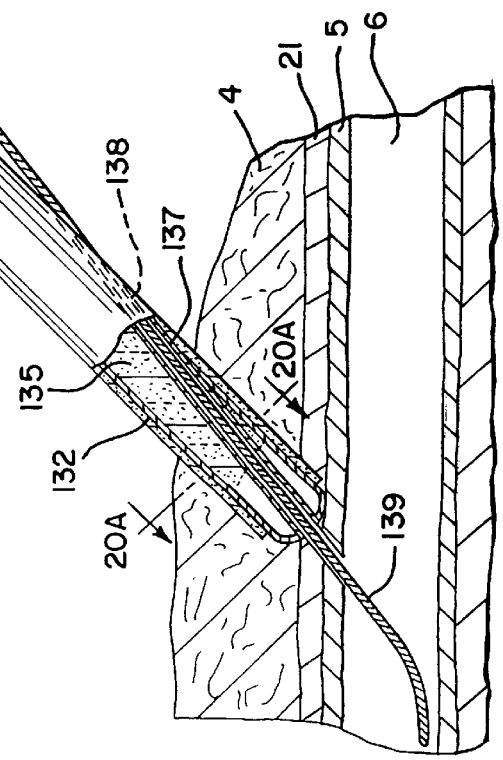

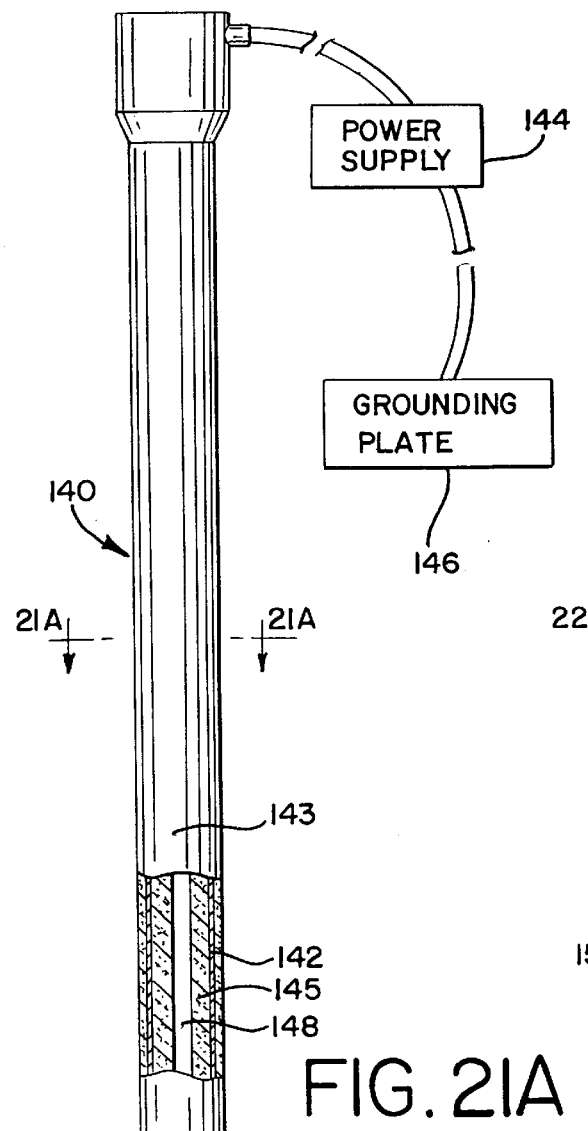
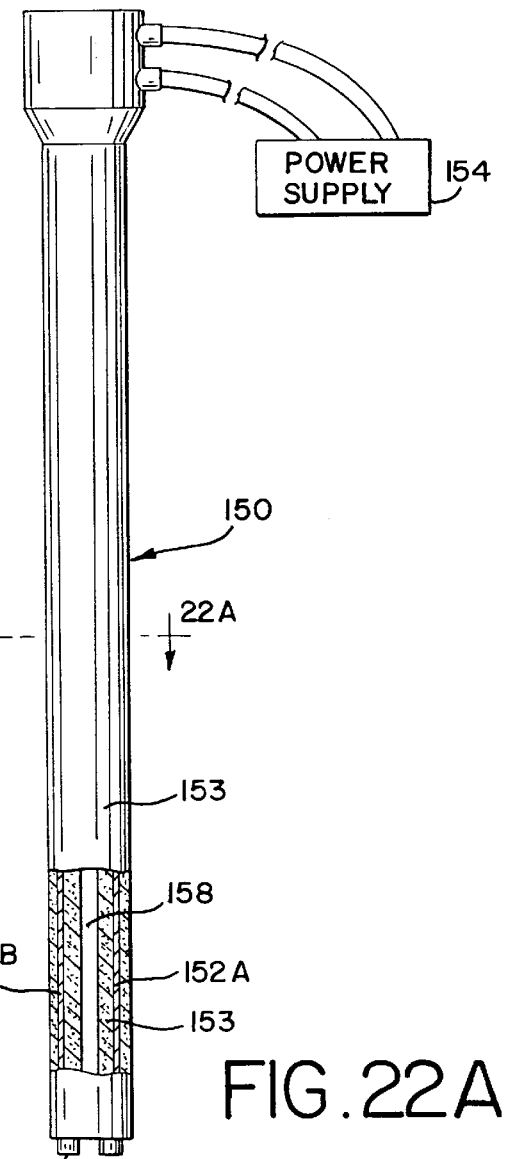
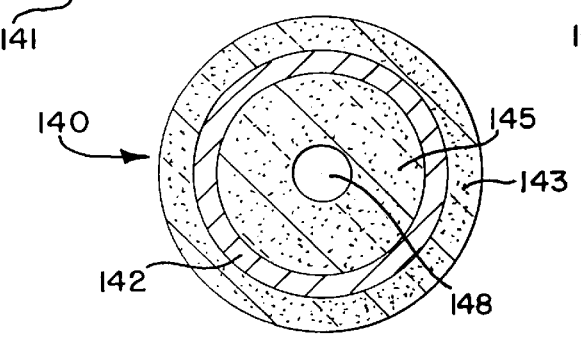
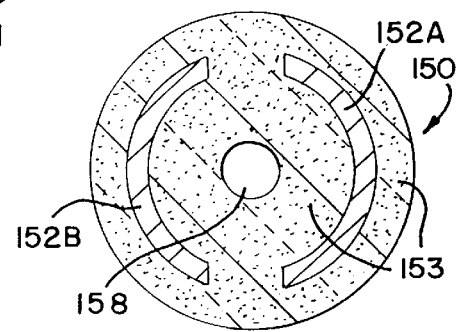

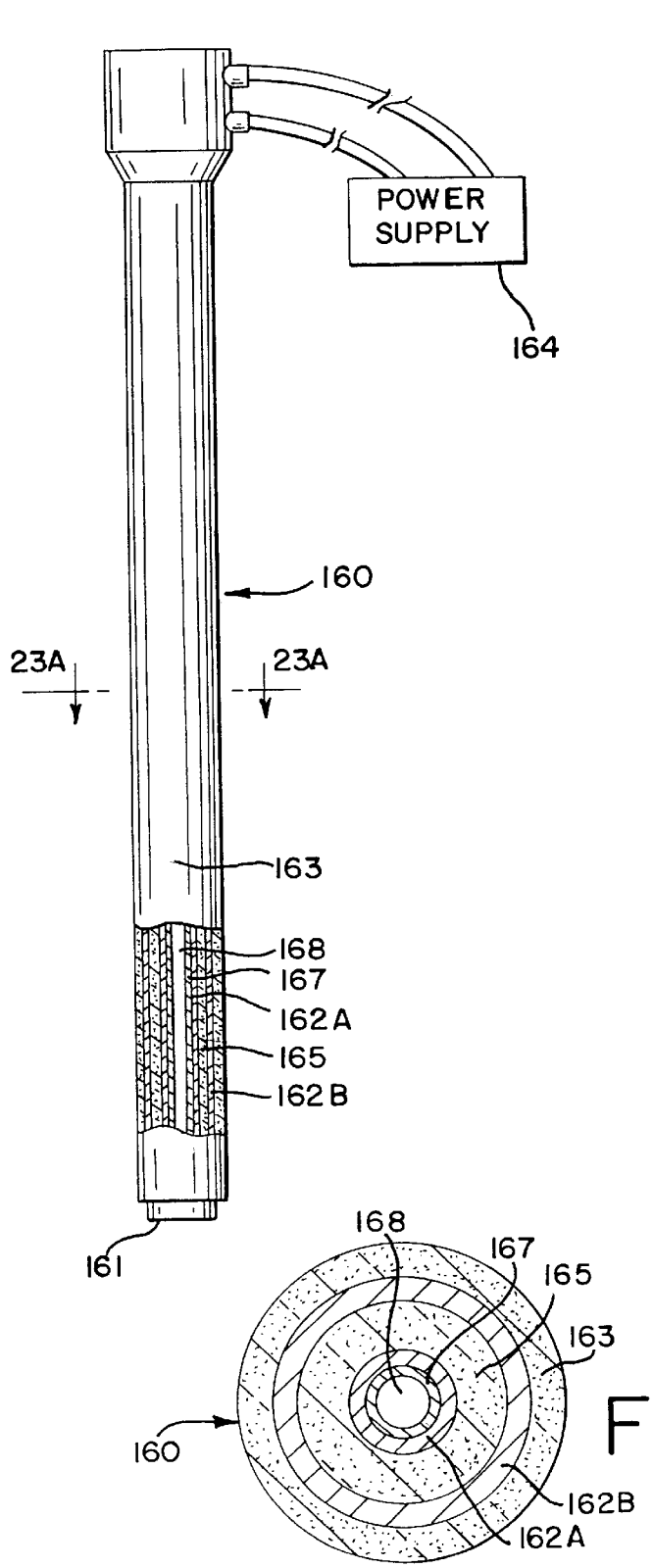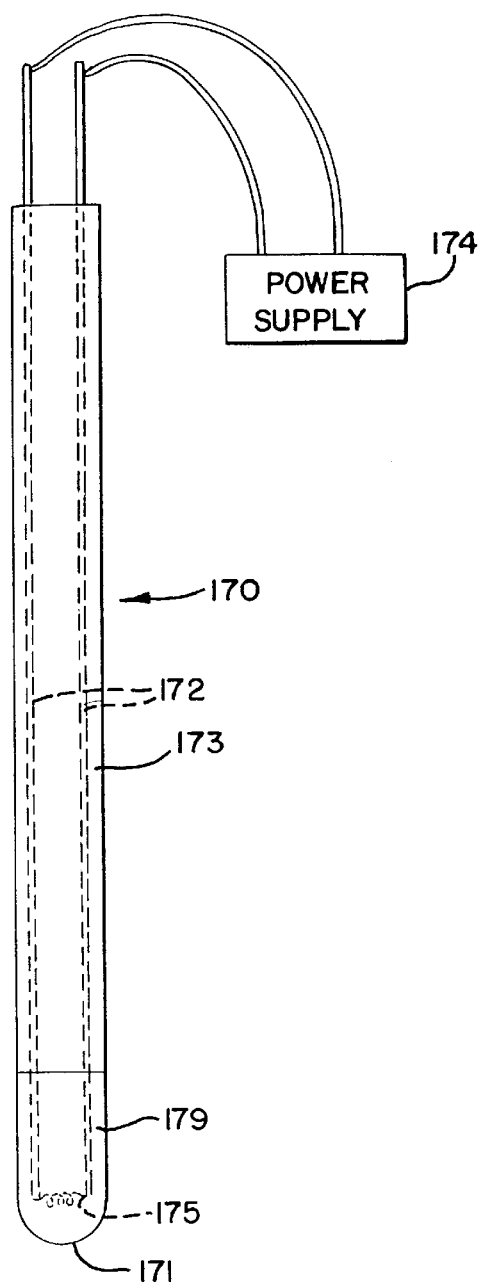
FIG. 23
FIG. 24
FIG. 23A

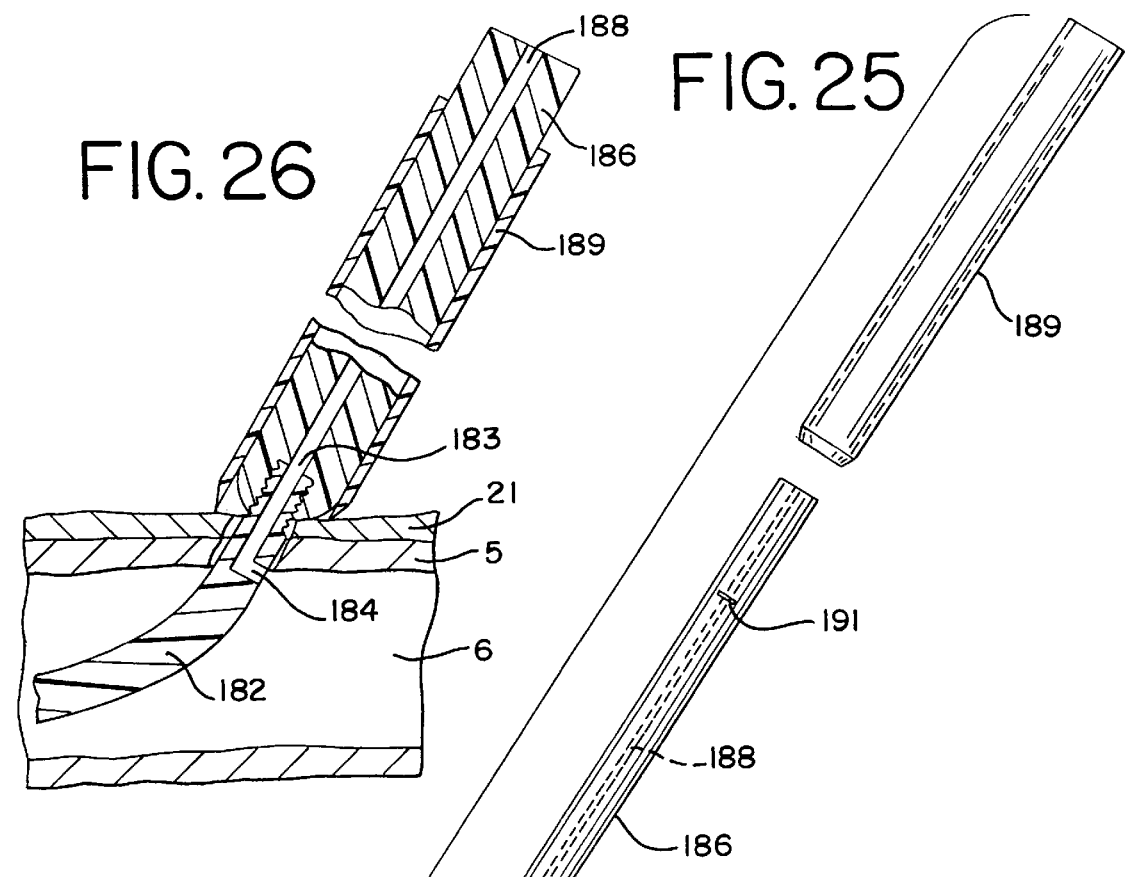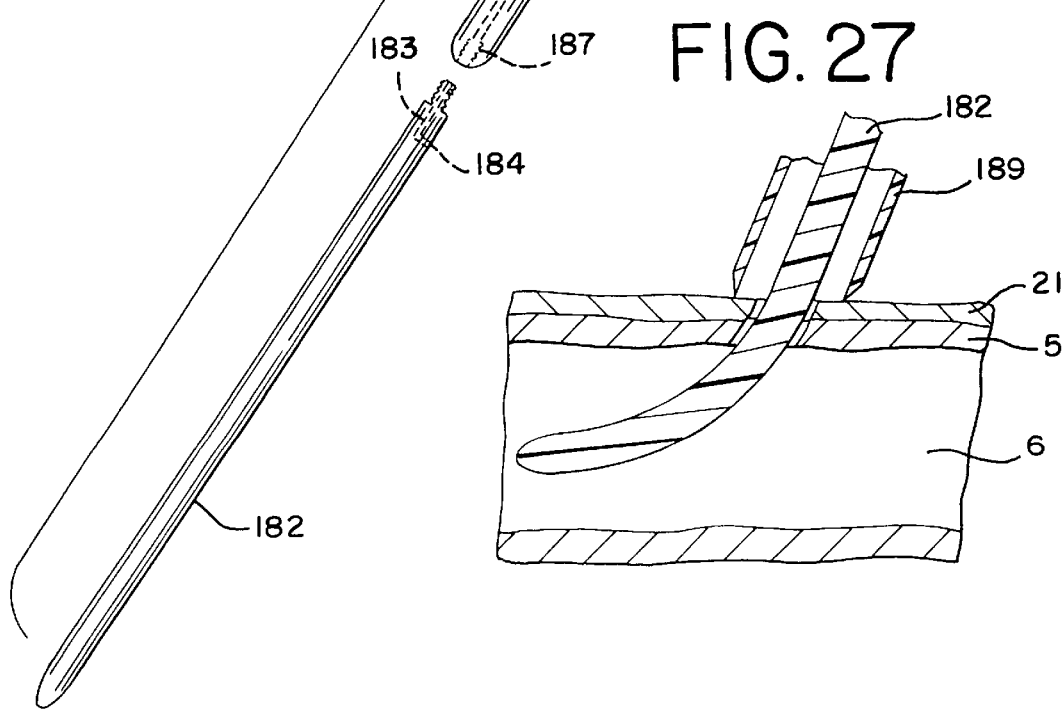

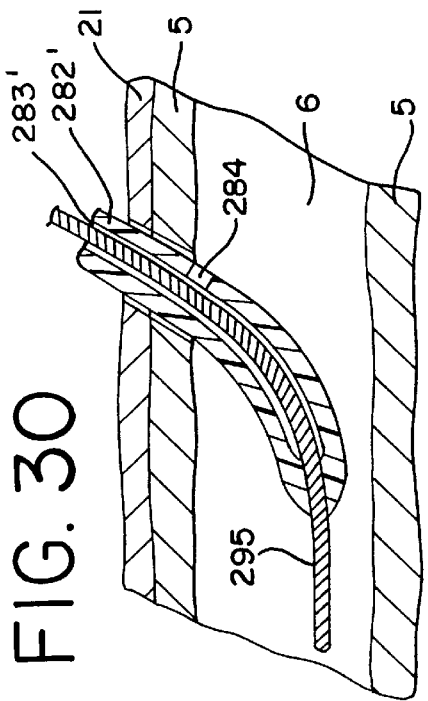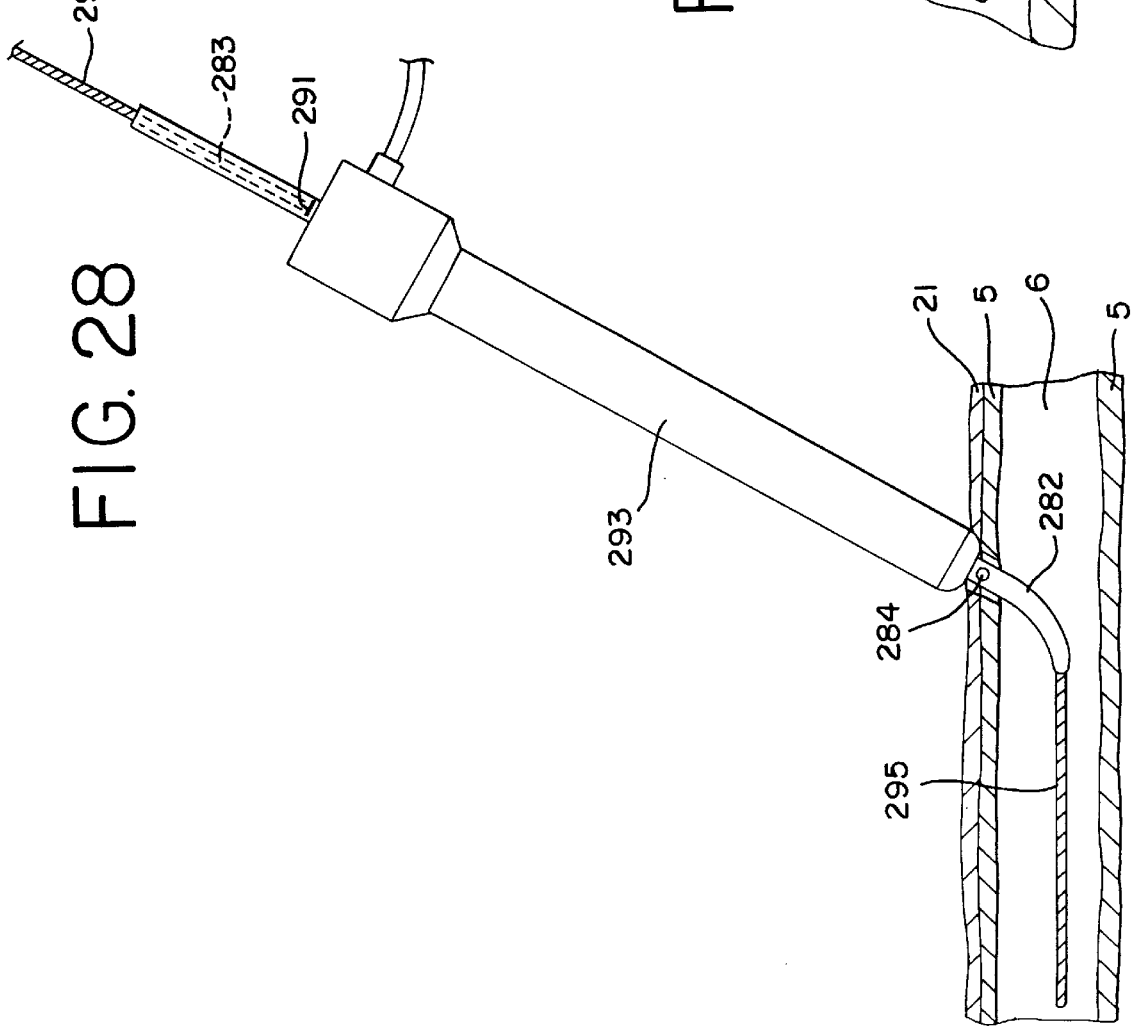

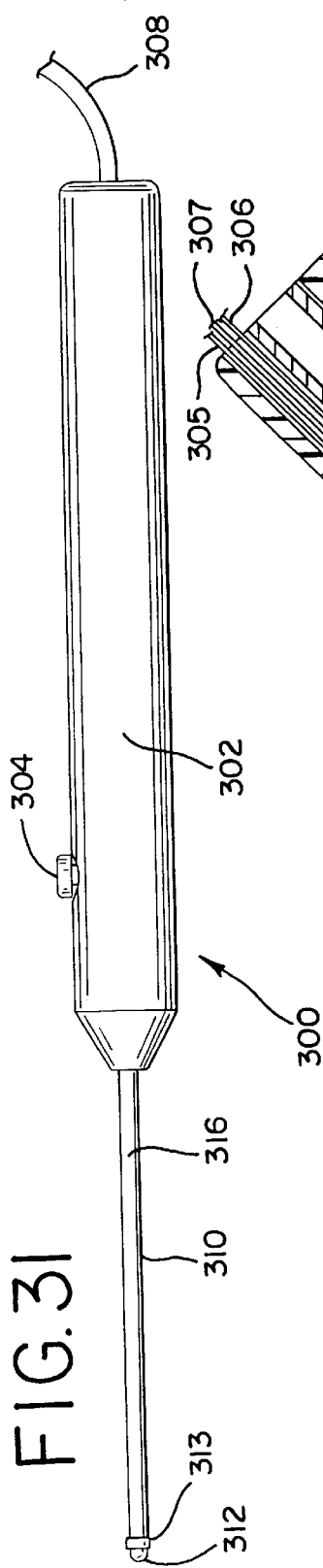
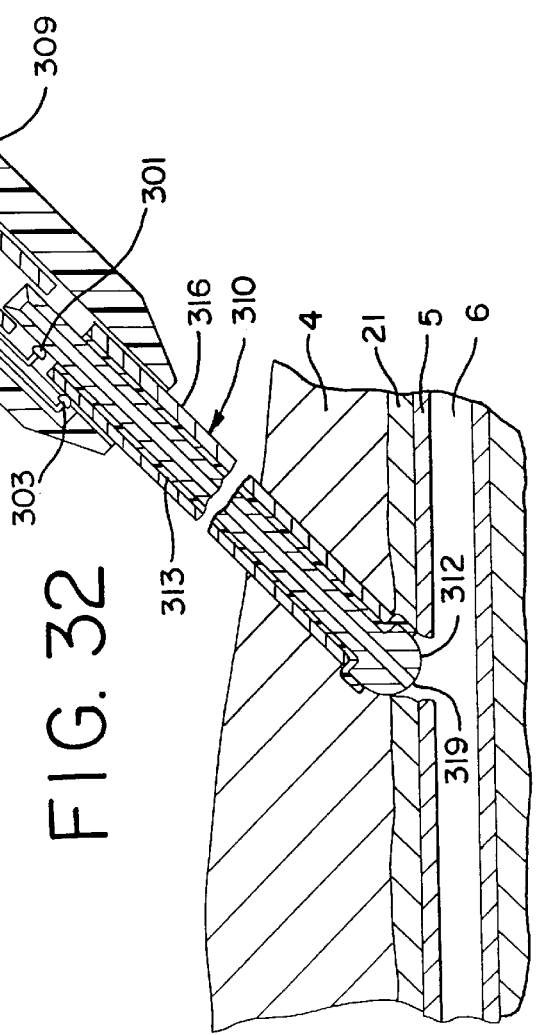
FIG. 31
FIG. 32

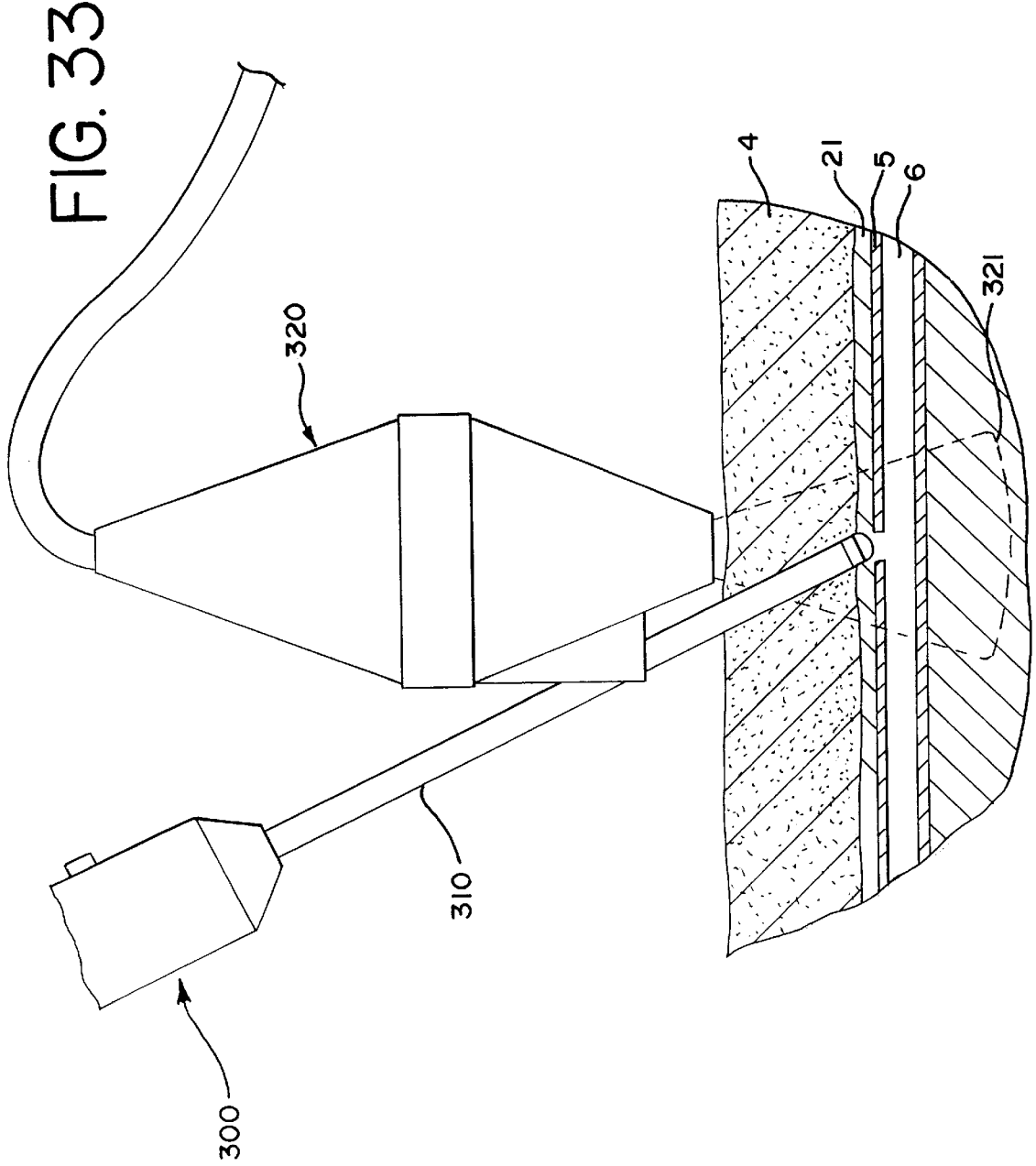

APPARATUS AND METHOD FOR SEALING VASCULAR PUNCTURES

CROSS REFERENCE TO RELATED APPLICATIONS

The present application is a continuation-in-part of application Ser. No. 08/055,634, filed Apr. 30, 1993, which is a continuation-in-part of application Ser. No. 07/873,955, filed Apr. 23, 1992, abandoned, and a continuation of Application Serial No. PCT/US93/10202, filed Oct. 22, 1993, which in turn is a continuation-in-part of said application Ser. No. 08/055,634. The disclosures of each of the above applications are hereby incorporated by reference.

FIELD OF THE INVENTION

The present invention relates to an apparatus and method for closing and sealing vascular punctures. More particularly, the present invention relates to a novel apparatus and method for sealing a vascular puncture resulting from the use of a medical device, catheter system or the like by using radio frequency or other energy to effect closure and thermal fusing of a puncture.

BACKGROUND OF THE INVENTION

Many medical procedures require access into the vascular system of the patient. Although various means may be used to obtain access into a vein or artery, typically access is obtained by inserting a cannula or introducer sheath through the skin and into the selected blood vessel. A medical device or diagnostic instrument, such as a guide wire, guiding catheter, balloon angioplasty device, atherectomy device, or the like is then inserted into the vascular system through the cannula or introducer sheath.

In percutaneous transluminal coronary angioplasty, for example, it is customary to introduce a catheter into the femoral artery at an entry site in a patient's leg and to advance the catheter through the artery to the coronary region. The artery, which may be located one half inch or more beneath the skin, is punctured with a needle or similar device. A guide wire is inserted through the needle and the needle is removed. An introducer sheath and dilator together are threaded over the guide wire. The introducer sheath is often twisted and otherwise manipulated as it is inserted into the vessel, thereby causing further enlargement of the vascular puncture. The dilator is then removed and the catheter is inserted.

To permit the insertion of a medical device or instrument therethrough, the introducer sheath must be of a relatively large diameter. Introducer sheaths typically have a diameter in the range between one millimeter and six millimeters, thus creating a significant puncture in the artery. After the intravascular medical procedure is completed, this puncture must be closed and bleeding from the blood vessel stopped.

At present, such bleeding is stopped by the application of direct digital pressure over the puncture site by a trained physician or other suitably trained medical personnel. Such direct pressure must be applied for a sufficiently long time for hemostasis to occur so that the opening is effectively closed and further bleeding is prevented. In the case of punctures into the femoral artery, the pressure is generally applied for twenty to thirty minutes, but it may be necessary to apply pressure for as long as one hour. Further, twelve pound sandbags may then be placed on the puncture site for an additional two to six hours.

The time required to stop bleeding using digital pressure is not an efficient use of medical professional services. Not only is this direct digital pressure application procedure wasteful of time by highly skilled medical professionals, the procedure results in a substantial reduction, if not virtual arrest, of blood flow through the vessel. Since thrombosis is one of the major problems that can occur in the immediate post-operative period, any reduction in blood flow, caused by the application of digital pressure, is undesirable. Furthermore, when digital pressure is applied, an undesirable bruise or hematoma can form at the entry site, since internal bleeding of the punctured artery continues until clotting blocks the puncture. There is also a significant chance that upon movement by the patient, the puncture will reopen and begin bleeding again, resulting in a hematoma or other complications. In addition, when anticoagulants used in the medical procedure are left active in the body, the introducer sheath is generally left inside the patient for twelve to twenty four hours in order for the anticoagulants to clear from the blood. Because the patient may be required to remain immobile and because of the risk of complications, patients are usually required to remain overnight in the hospital for observation, thus greatly increasing the cost of the overall procedure.

One prior device for stopping bleeding from a puncture in a blood vessel is a type of expandable plug. An example of such a device is shown in U.S. Pat. No. 4,890,612 (Kensey). The plug is pushed through the puncture into the blood vessel and into the blood stream. Once exposed to blood, it expands. The expanded plug is then pulled back against the puncture where, because of its expanded size, it plugs the opening. A similar device is an expandable closure, such as that described in U.S. Pat. No. 4,852,568 (Kensey). Such devices may work satisfactorily, but require inserting and leaving a foreign object in the vessel for a period of time. It is usually medically preferable to avoid leaving objects in a vessel, even if they eventually biodegrade.

Another device for stopping bleeding from a puncture is disclosed in U.S. Pat. No. 4,929,246 (Sinofsky). This patent relates to a method for closing an artery using laser energy while simultaneously applying pressure directly to the artery through the use of a balloon placed on the exterior of the artery over the puncture site.

SUMMARY OF THE INVENTION

An apparatus for closing and sealing a puncture at a puncture site in a vessel located beneath the skin using radio frequency or other energy to cauterize the puncture has been developed. In one aspect, the invention constitutes a probe sized to be percutaneously inserted adjacent the vascular opening and a connector for connecting the probe to an energy supply source; the probe being configured to conduct energy directly to tissue adjacent the probe to cause heating of tissue surrounding the vascular opening to close the opening.

In another aspect, the apparatus comprises a cautery device having a means for forcing together biological tissue surrounding a percutaneous vascular puncture and at least one electrode connectable to a radio frequency power source such that an electrical current may flow through the tissue, thermally fusing the tissue together.

In yet another aspect, the invention is an apparatus for the percutaneous medical treatment of biological tissue, comprising a plurality of electrodes connectable to a radio frequency power source, the electrodes adapted to engage biological tissue at spaced points; and a lumen connected to the electrodes for guiding the electrodes to the biological tissue at said spaced points.

In one specifically disclosed embodiment, the apparatus comprises a radio frequency cautery device having forceps adapted to grasp vascular tissue surrounding the puncture site. The forceps, when connected to a radio frequency power source, also serve as bipolar electrodes for fusing the tissue surrounding the puncture.

A backstop element, such as a balloon occluder assembly or a T-shaped occluder, may also be used in conjunction with the cautery device. The balloon occluder assembly essentially comprises a balloon at the distal end of a balloon shaft and a means for inflating the balloon. The balloon occluder assembly temporarily occludes the puncture while providing a backstop against which the forceps may grasp the vascular tissue. The balloon occluder assembly also has utility separate from its use with the disclosed cautery device, as discussed more fully hereafter.

In another aspect, the invention is a method of sealing a vascular opening comprising the step of delivering energy to the vascular wall, resulting in local heating of bodily material external to the intima layer of the vessel to achieve hemostasis without substantially heating the intima layer of the vessel.

In yet another aspect, the method of the invention comprises the steps of percutaneously inserting a probe adjacent to the vascular opening; conducting energy from the probe directly to tissue adjacent the probe in an amount sufficient to cauterize the tissue to thereby close the vascular opening; and removing the probe. The invention in still another aspect is a method of sealing a vascular puncture comprising the steps of holding the vascular tissue surrounding the puncture site in a contacting position and applying energy to that tissue, the energy being sufficient to thermally fuse the tissue together, thus sealing the puncture. Preferably, this method of sealing a puncture includes the steps of advancing a balloon into the lumen of a vessel, inflating the balloon and withdrawing it to abut the puncture from within the vessel, inserting a cautery device having forceps connected to a radio frequency power source, grasping and bringing the vascular tissue into a contacting position, causing an electrical current to flow from one forceps, through the vascular tissue, to the other forceps, thus effecting a closure by thermally fusing the vascular tissue together.

In another aspect of the invention, a balloon occluder need not be used. Instead, pressure is applied to the vessel to restrict blood flow therethrough, an electrode is percutaneously inserted to a position proximate the puncture site, and radio frequency energy is used to cause thrombosis of the blood to seal the puncture site.

The present invention thus provides an apparatus which is simple to use and which overcomes the disadvantages of the prior art, including the need for the application of digital pressure for long periods of time and the possibility of a substantial reduction of blood flow through the vessel. The present invention also provides methods that are effective for closing off a puncture or other opening in a blood vessel by using radio frequency or other energy to thermally fuse the vascular tissue or form a seal by causing thrombosis of the blood. The puncture is hemostatically sealed almost immediately after the medical procedure is performed, thus avoiding any potential complications associated with re-opening of the puncture or long hospital stays while anticoagulants remain active in the body.

The forgoing has outlined rather broadly the advantages of the present invention. Additional benefits of the invention will be described hereinafter. These advantages, as well as the invention itself, are more easily understood in view of the attached drawings, a brief description of which follows.

BRIEF DESCRIPTION OF THE DRAWINGS

FIG. 6 through FIG. 8 illustrate alternate embodiments of the actuating mechanism.

FIG. 9 through FIG. 18 are partial cross-sectional views illustrating the method of using the first preferred embodiment of the present invention.

FIG. 9A is a partial cross-sectional view taken along line 9A—9A of FIG. 9 showing the relationship of the arterial sheath to the femoral artery and associated anatomy.

FIG. 15A is an enlarged cross-sectional view of the region of FIG. 15 showing the various layers of the vascular tissue being contacted by the electrodes.

FIG. 17A is an enlarged cross-sectional view of the region of FIG. 17 where the seal is made.

FIG. 19A and 19B illustrate an alternate embodiment of the backstop element of the present invention.

FIG. 20 illustrates a second apparatus embodiment of the present invention.

FIG. 20A is an enlarged cross-sectional view taken along line 20A—20A of FIG. 20.

FIG. 21 illustrates a third apparatus embodiment of the present invention.

FIG. 21A is an enlarged cross-sectional view taken along line 21A—21A of FIG. 21.

FIG. 22 illustrates a fourth apparatus embodiment of the present invention.

FIG. 22A is an enlarged cross-sectional view taken along line 22A—22A of FIG. 22.

FIG. 23 illustrates a fifth apparatus embodiment of the present invention.

FIG. 23A is an enlarged cross-sectional view taken along line 23A—23A of FIG. 23.

FIG. 24 illustrates a sixth apparatus embodiment of the present invention.

FIG. 25 is an exploded view of a first alternative vessel depth locating and occluding apparatus of the present invention.

FIG. 26 is a partial cross-sectional view of the apparatus of FIG. 25 in use.

FIG. 27 is another partial cross-sectional view like FIG. 26 showing the apparatus of FIG. 25 ready for insertion of a cautery probe.

FIG. 28 illustrates a second alternate embodiment of a vessel depth locating and occluding apparatus and one of the earlier described cautery devices of the present invention.

FIG. 29 is an enlarged cross-sectional view disclosing a first alternative embodiment of the apparatus of FIG. 28.

FIG. 30 is an enlarged cross-sectional view disclosing a second alternative embodiment of the apparatus of FIG. 28.

FIG. 31 illustrates a seventh apparatus embodiment of the present invention.

FIG. 32 is a cross-sectional view of the apparatus of FIG. 31 in place for a cautery procedure.

FIG. 33 is a schematic representation of the use of ultrasound to verify placement of the cautery apparatus of FIG. 31.

DETAILED DESCRIPTION OF THE DRAWINGS AND PREFERRED EMBODIMENTS OF THE INVENTION

Before describing the apparatus of the present invention, a brief description of a typical intravascular surgical procedure, e.g., catheter instrumentation of an artery using a percutaneous incision or puncture, will be given to best appreciate the features of the cautery apparatus of the present invention. In such a procedure a cannula of an instrument, such as an angiographic needle, is inserted percutaneously through the skin and arterial sheath and into the artery. The needle cannula of an instrument is held in place and the flexible end of a guide wire is then passed through the cannula into the artery to the desired depth (i.e., longitudinal position therealong). Once the guide wire is in place, the needle cannula is removed leaving the guide wire in place. A conventional introducer sheath combined with an arterial dilator are then passed over the guide wire, through the puncture and into the artery. The guide wire and the dilator are then removed, leaving the sheath in place. The catheter is then inserted through the introducer sheath and threaded down the artery to the desired intravascular location, e.g., the situs of the atherosclerotic occlusion, usually the coronary region. Once the intravascular procedure has been completed, the catheter is removed. Thereafter, once anticoagulants have been inactivated or cleared from the body, the usual procedure has been to remove the sheath and to have a surgeon or other trained person apply digital pressure to the percutaneous puncture until hemostasis has occurred. As noted above, the stopping of bleeding from a puncture was previously a difficult and time consuming task.

As used herein, and in the appended claims, the term "puncture" means a partial opening in the vessel wall made to gain access to the vessel, and includes openings made by a needle, dilator, introducer, scissors, scalpel, blade or otherwise.

The apparatus of the present invention effects the hemostatic closure of a percutaneous or other type of puncture, incision or opening in a body vessel without necessitating the application of digital pressure thereto. In accordance with the preferred embodiment of the present invention, the introducer sheath is left in place after the catheter is removed and a balloon occluder is advanced through the introducer sheath into the vessel lumen. In additional preferred embodiments, any backstop element, such as a T-shaped occluder, can be used to support the tissue surrounding the puncture. A cautery device having forceps which are connected to a radio frequency power source are then inserted into the skin to the puncture site, where the forceps grasp the vascular tissue surrounding the puncture. The balloon or T-shaped occluder is withdrawn and the device is then energized, causing a cauterizing discharge to sass from the device to the vascular tissue surrounding the puncture, thereby thermally fusing the puncture.

Figure 1:
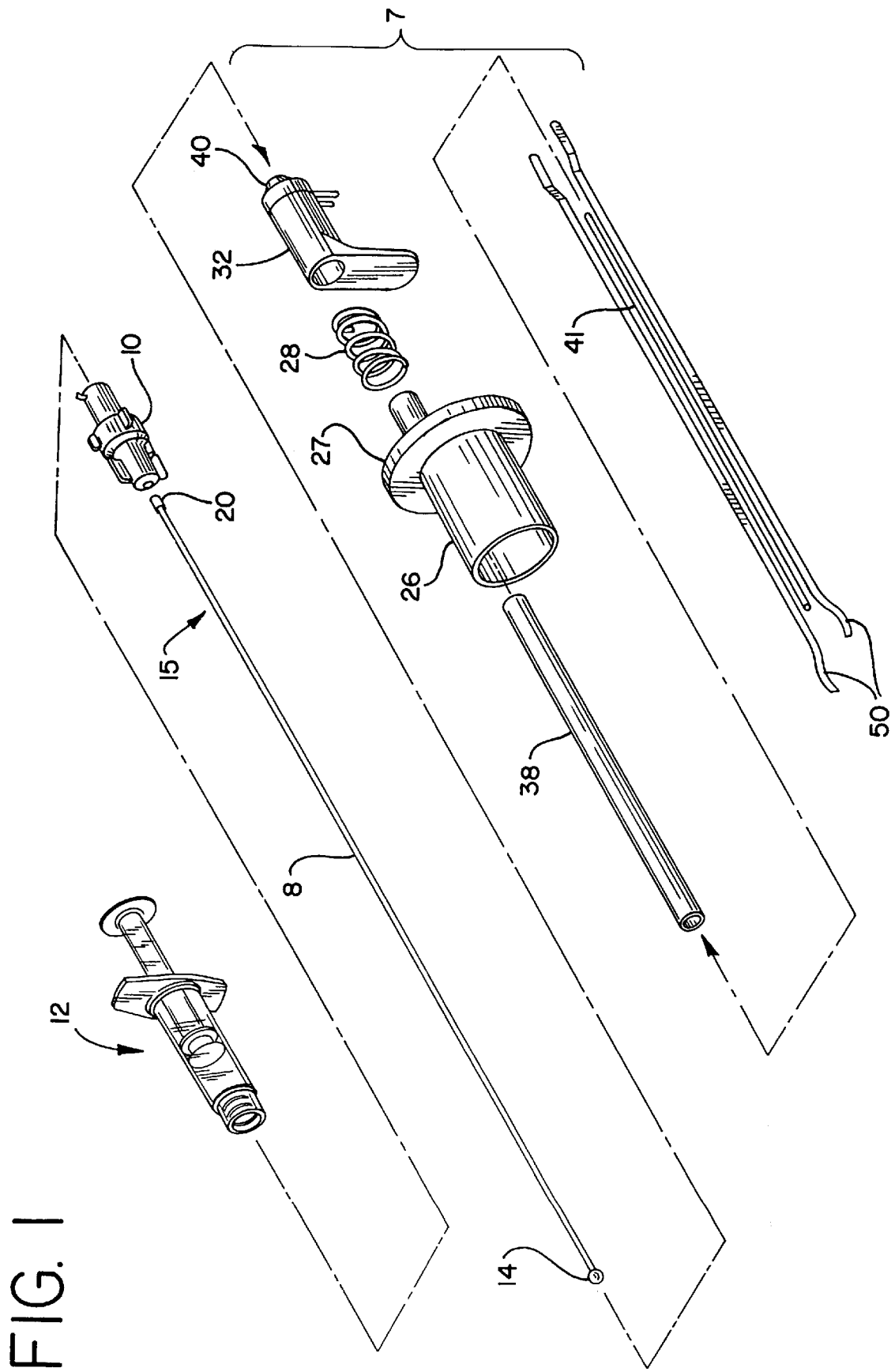
FIG. 1 is an exploded view of the first preferred apparatus embodiment of the present invention.

Referring now in greater detail to the various figures of the drawing, wherein like reference characters refer to like parts, FIG. 1 generally illustrates a cautery apparatus of the first preferred embodiment. This apparatus consists essentially of three components: a cautery device 7, a balloon occluder assembly 15 and a radio frequency power source (not shown). The apparatus functions to close and seal a puncture or other opening in a blood vessel, duct or lumen in a living being. The apparatus thus has particular utility when used in connection with intravascular procedures such as angioplasty and other types of recanalization of atherosclerotic arteries, etc. However, it should be appreciated that the apparatus can be used to hemostatically close a puncture or other opening within a body. Thus, it is to be understood that while the description of the invention contained herein is directed to closing and sealing percutaneous punctures in vessels, the apparatus has other applications.

The cautery device or probe 7 of the first preferred embodiment comprises a gripping handle 26, a tubular retaining housing 38, a spring 28, a thumb rest 32, forceps 50, a cap 40, an inner tubular housing 41 and detachable electrical leads 42. The gripping handle 26 is preferably cylindrical, but may be of any shape or size which allows it to be conveniently grasped with one hand. The gripping handle 26, for example, may incorporate an outwardly projecting annular ledge 27 or any other additional element which allows it to be easily grasped and held. The gripping handle 26, as well as the cap 40 and the thumb rest 32, can be constructed from any suitable material, preferably a lightweight plastic, such as polycarbonate or acrylonitrile-butadiene-styrene copolymer (ABS). The cap 40 is located at the proximal end of the thumb rest 32 and provides outlets for the balloon shaft 8 and the detachable electrical leads 42.

In the first preferred embodiment, the thumb rest 32, the spring 28 and the gripping handle 26 comprise the actuator element. While holding the gripping handle 26, the thumb rest 32 is used to oppose the spring force of the spring 28, actuating the forceps 50. Actuating the forceps 50 causes the forceps to move from a first stored position to a second open position, as discussed more fully hereafter.

The tubular retaining housing 38, the distal end of which is also referred to as an elongated cautery probe or a cautery probe tip, is preferably an elongated, thin-walled tube or lumen made of any common plastic, including but not limited to PTFE, polyethylene, polyurethane, polycarbonate, polyester, nylon or ABS. The wall of the housing 38 is preferably 0.010" thick, but may be between 0.005" and 0.030". The inner diameter of the housing 38 is preferably about 0.158" and may vary from approximately 0.010" to 0.250". The tubular retaining housing 38 has an inner tubular housing 41 inside, which provides a guide lumen. The inner tubular housing 41, along with the tubular retaining housing 38, are used to guide the forceps 50 to the puncture site.

Detachable electrical leads 42 connect the proximal end of the forceps 50 to the power source, allowing the forceps 50 to act as electrodes. Any connector element, however, that connects the forceps to the power supply is contemplated by the present invention. Further, the connector element may also include an activating switch element, such as a thumb switch, which allows the electrical current to flow only when said switch element is activated. Alternatively, a foot switch associated with the power source may be used. The activating switch element may also include a timing feature which allows the physician to energize the device for a predetermined amount of time, regardless of how long the switch element is engaged.

Figure 2:
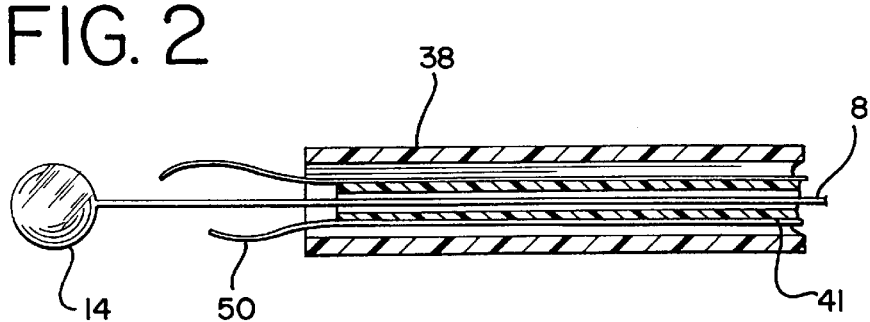
FIG. 2 is an enlarged cross-sectional view of the distal portion of the device of the first preferred embodiment.
Figure 3:
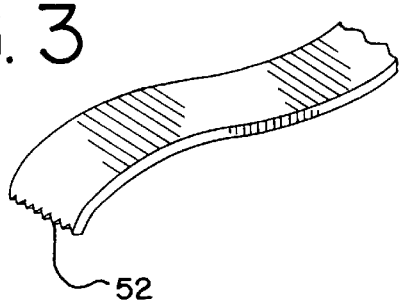
FIG. 3 is an enlarged perspective view of the distal end of a forceps of the first preferred embodiment.
Figure 4:
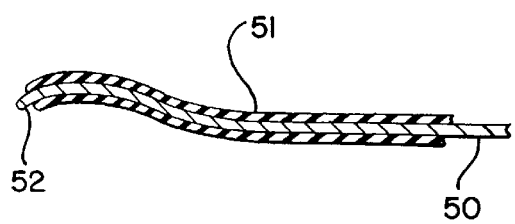
FIG. 4 is an enlarged cross-sectional view of the distal end of a forceps of the first preferred embodiment.
Figure 14:
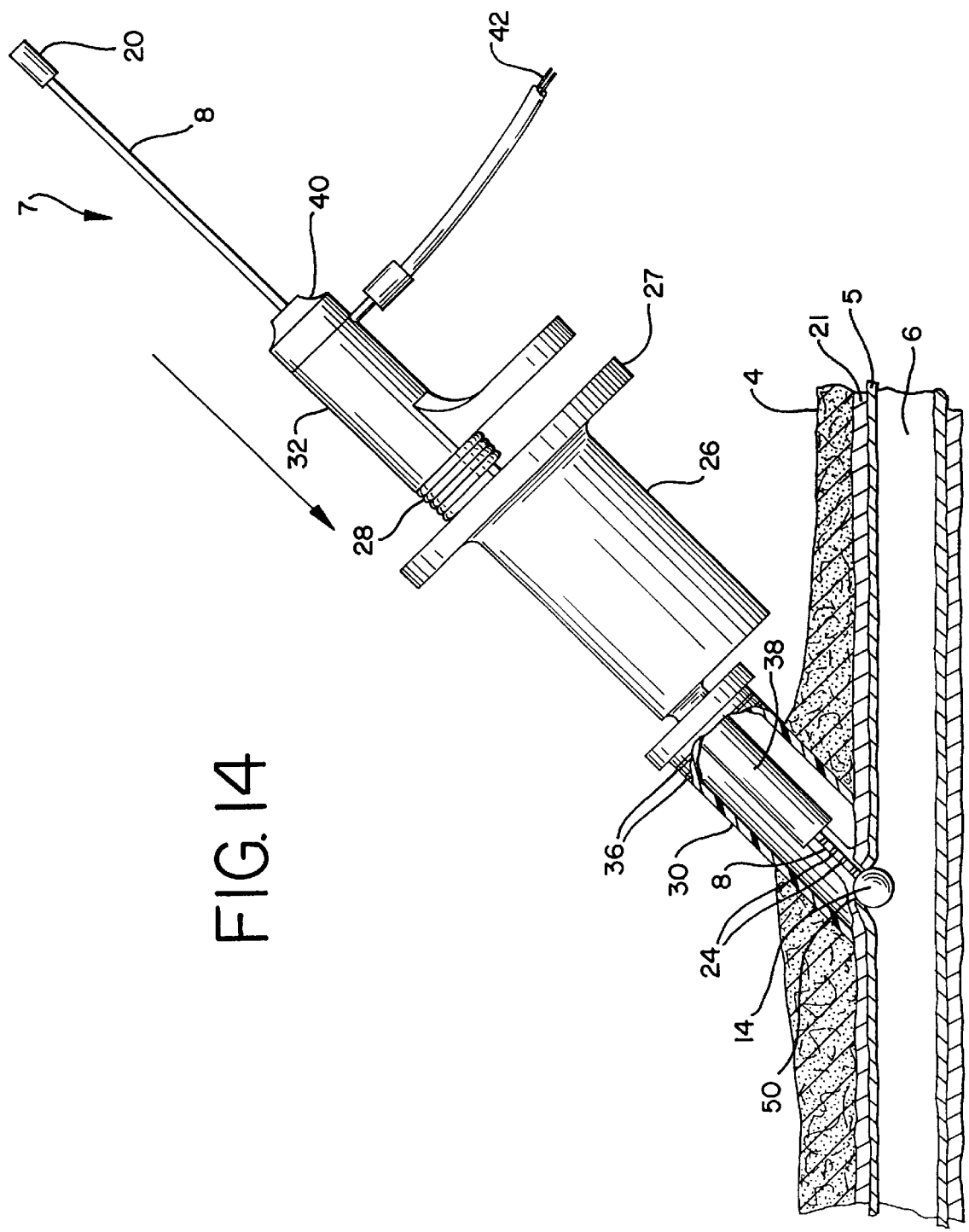

In their first position, the forceps 50 reside substantially inside the tubular retaining housing 38 (FIG. 2). The forceps 50 are insulated, preferably with plastic insulation 51, except for the distal end where the gripping of tissue occurs (FIG. 4). Any suitable insulating material may also be used. The distal end of the forceps 50 of the first preferred embodiment form an arc of approximately 160° and have a serrated gripping portion 52 (FIG. 3). The forceps are preferably up to 2 mm wide at their gripping portion 52. The gripping portion 52 of the forceps 50 will preferably almost touch when just outside the distal end of the tubular retaining housing 38. When in use, the vascular tissue is disposed in this gap. The forceps 50 are preferably uneven in length to accommodate the angle of entry of the cautery device 7 into the skin (as shown in FIG. 14), the angle ideally being 45° to the surface of the vessel. For additional preferred embodiments, the forceps are preformed into any shape that is advantageous for gripping tissue and may be of even or uneven length. The forceps 50 are preferably made of a metal alloy such as Elgiloy™, manufactured by Elgiloy Partnership, Ltd., MP-35N™ or hardened stainless steel, but may be made of any material suitable for the purpose of gripping biological tissue.

Preferably, the forceps comprise bipolar electrodes. Thus, at any one time, one forceps will function as the anode and the other as the cathode. Although the first preferred embodiment contemplates the use of only two forceps, embodiments including a plurality of forceps are also contemplated. In these embodiments, the firing or activating of the current can be controlled electronically to occur in sequence.

As best shown in FIGS. 1 and 2, the inner tubular housing 41, also referred to as a guide lumen, is a thin tube preferably made of any common plastic, including but not limited to PTFE, polyethylene, polyurethane, polycarbonate, polyester, nylon or ABS. It is located between the substantially parallel arm portions of the insulated forceps 50 and extends through the gripping handle 26 and the tubular retaining housing 38. The inner tubular housing 41 allows the balloon shaft 8 of the balloon occluder assembly 15 to pass through the forceps 50 and out through the proximal end of the cautery device 7. In additional preferred embodiments, conventional triple lumen tubing comprising an inner hollow tube connected to the inside of an outer hollow tube by two longitudinally extending flat sections can be used in place of the combination of the tubular retaining housing 38 and the inner tubular housing 41. The triple lumen tubing is advantageous in that it isolates the forceps from each other and from the balloon shaft and avoids the need for constructing the tubular retaining housing 38 and the inner tubular housing 41 from separate elements.

The balloon occluder assembly 15 of the first preferred embodiment consists of a elongated balloon shaft 8 having spaced markings 24 on the distal portion thereof, a balloon 14 at the distal end of shaft 8, a check valve assembly 20 on the proximal portion of the shaft 8, a removable hub 10 and a syringe 12.

The balloon shaft 8 is essentially a thin tube or lumen made of plastic or metal. The balloon shaft has an outer diameter of approximately 0.050" and an inner diameter of approximately 0.040". The balloon 14, disposed at the distal end of the balloon shaft 8, may be made with any suitable material including, but not limited to, latex (natural or synthetic), polyurethane, silicone, polyethylene terephthalate (PETP), polyvinyl chloride, polyethylene and polyethylene copolymer, and may be compliant or noncompliant. Preferably, the balloon is made from a high density polyethylene and is preferably shaped in the form of a flat disk, though spherical and cylindrical forms are also acceptable. The balloon may be of any shape and size suitable to occlude the puncture being sealed. The balloon 14 may also be fitted with a balloon protector (not shown). The protector is a lumen or tube, made of plastic, PTFE, PETP or any other suitable material, which fits around the balloon 14 to protect the balloon from being torn or ripped and also, if necessary, to alter the shape of the inflated balloon by radially compressing certain areas of the balloon.

Figure 5:
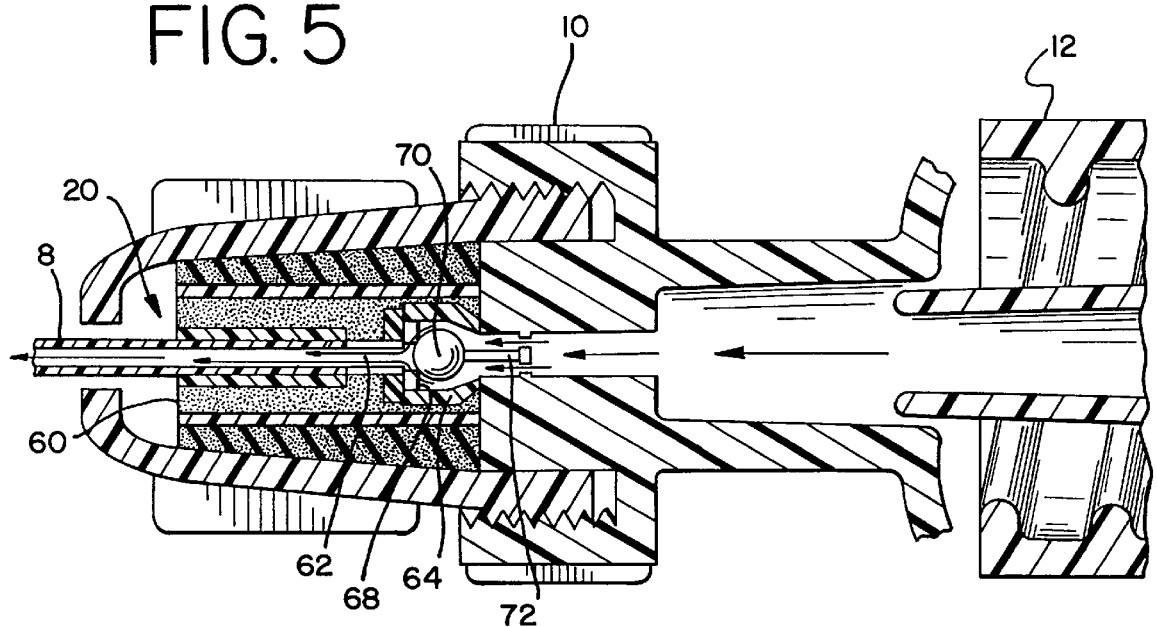
FIG. 5 is an enlarged cross-sectional view of a check valve assembly and hub used in conjunction with the inflation means of the first preferred embodiment.

The check valve assembly 20 at the proximal end of balloon shaft 8 provides a means for inflating and keeping the balloon 14 inflated for the desired period of time. The diameter of both the balloon shaft 8 and the check valve assembly 20 is preferably smaller than approximately 0.12 inches (9 French), although both can be of any size which allows the cautery device to be easily inserted over them. As best seen in FIG. 5, the preferred embodiment of the check valve assembly 20 consists essentially of housing 60 into which the proximal end of the balloon shaft 8 enters, an air passage 62 connecting the balloon shaft 8 to a chamber 64. The chamber 64 has a conical portion at the proximal end and a shelf 68 at the distal end thereof. The chamber also contains a spherical member 70, which is movable between a first and second position within the chamber 64. When in a first position (as shown in FIG. 5), the spherical member 70 is in a contacting position with the shelf 68, which prevents the spherical member 70 from blocking the air passage 62. The spherical member 70 is held in this position by the pin element 72, discussed below. Thus air is allowed to pass through the assembly to inflate or deflate the balloon 14. At a second position, the spherical member 70 lodges against the conical portion of the chamber 64, completely preventing any air from passing through the assembly. Also contemplated by this invention are other conventional check valve assemblies.

A removable hub 10 with a standard female luer fitting is adapted to attach to the check valve assembly 20. The hub 10 generally provides a means for deflating the balloon 14, and, in conjunction with a syringe 12, for inflating the balloon. In the first preferred embodiment, a pin element 72 in the hub 10 provides a means for moving the spherical member 70 of the check valve assembly 20 from a position where it blocks the flow of air through the assembly to a position where the flow of air is unimpeded. The hub 10 may be made from any suitable material, such as polycarbonate or high-density ABS, and may be of any shape and size suitable for accomplishing the desired task.

A syringe 12 attaches to the removable hub 10 via a standard female luer fitting on the proximal end of the hub 10 and provides a means for inflating the balloon 14. Preferably, a 1 ml syringe is used. A liquid or a gas may be used to inflate the balloon 14, though a solution of saline is preferable.

A suitable radio frequency power source (not shown) is the Wet Field II made by Mentor O&O, Inc. The power source may be either alternating current (AC) or direct current (DC).

The cautery apparatus of the first preferred embodiment also includes other secondary components, such as a conventional introducer sheath 2, a dilator 34, a cautery sheath 30 and an introducer (not shown). The introducer sheath 2 comprises a hollow tube which extends into the vessel lumen 6 (FIG. 9). It is left in the artery after the catheterization or other percutaneous intravascular procedure and is standard and well known in the art. It is generally made from a suitable, flexible material, such as polyurethane, PTFE or polyethylene. Typical introducer sheaths range in diameter from 5 to 20 French and contain a diaphragm at the proximal end thereof to prevent the fluid in the lumen of the vessel from escaping through the sheath 2 once it is inserted into the vessel. Any suitably sized and constructed introducer sheath may be used.

The introducer (not shown), which is also conventional, is a small hollow tube having a tapered distal end. The introducer is adapted to be inserted into the proximal end of the introducer sheath 2. The introducer spreads apart the walls of the diaphragm in the introducer sheath 2 to allow a portion of an instrument, such as a guide wire, to be inserted into the introducer sheath without damaging the instrument. When used in practicing the method of the present invention, the introducer is used to allow insertion of the distal end of the balloon occluder assembly, which contains a relatively fragile balloon 14, into the introducer sheath and hence into the vessel lumen 6.

The cautery sheath 30 is similar to the introducer sheath 2, except that it is larger in diameter and not designed to extend into the vessel lumen 6 (FIG. 12). The cautery sheath 30 is a hollow tube which is adapted to be inserted into the skin after the introducer sheath 2 has been removed and around the balloon shaft 8 already in place. The cautery sheath 30 spreads and holds the skin and subcutaneous tissue above the vascular puncture away from the balloon shaft 8 and allows the tubular retaining housing 38 containing the forceps 50 to be inserted into the body without contacting the surface of the skin or any subdermal tissue. It may be made of any suitable material including polyethylene, polyurethane and PTFE and may have an inner diameter of approximately 0.10 inches to 0.250 inches, but in any case must be larger in diameter than the tubular retaining housing. The cautery sheath 30 of the first preferred embodiment is capable of spreading the tissue to an opening dimension that is both larger than the opening in the vessel wall and larger than the dimension of the portion of the energy delivery probe used to contact the tissue surrounding the opening. The cautery sheath 30 is also generally about 3–4 inches in length. The distal end of the cautery sheath 30 is preferably cut at a 45° angle, but any suitable angle is also acceptable. The cautery sheath 30 has markings 36, which correspond to the markings 24 on the balloon shaft 8. These markings could be numbers or a sequence of color bands. Also contemplated are other marking systems where the physician is able to identify and locate the exact depth of the puncture.

The dilator 34 is a hollow tube portion having a blunted tapered distal end portion (FIG. 12). The tapered distal end is adapted to be inserted into the skin above the puncture site and over the balloon shaft 8 to gradually spread the skin apart. The tapered distal end is blunted, however, so that it abuts the exterior surface of the vessel surrounding the puncture. The dilator 34 is generally longer than the cautery sheath 30 so that it may be conveniently removed from the cautery sheath. Prior to insertion into the skin, the dilator 34 is fitted inside the cautery sheath 30, with the blunted tapered distal end of the dilator extending beyond the distal end of the cautery sheath. In use, the distal end of the dilator 34 is inserted first, followed by the distal end of the cautery sheath 30. Once the cautery sheath 30 is in place, i.e., its distal end contacting the exterior surface of the vessel wall, the dilator 34 is removed (FIG. 12).

The cautery device 7, the balloon occluder assembly 15 and all the secondary components mentioned above may be disposed of after one use. The power supply, however, may be reused.

Generally, the present invention contemplates various methods of using radio frequency and other energy to seal a percutaneous vascular puncture. Operation of the first preferred embodiment of the cautery apparatus may be explained with reference to FIGS. 9–18.

FIG. 9A shows the location of the vascular sheath 21 with respect to the vessel wall 5, in this case the femoral artery. The vascular sheath 21 is actually made of an outer layer 22 that comprises collagen, a fatty layer 23 and a thin connective tissue 25 in contact with the artery wall 5. At the point in the body where punctures are made for percutaneous transluminal coronary angioplasty procedures, the outer layer 22 of the arterial sheath 21 is actually a continuation of the iliac facia combined with the facia transversalis, which come together at the femoral triangle to form the sheath. The fatty layer 23 is a funnel shaped areolar tissue which encapsulates the vascular bundle (the femoral artery 6, the femoral vein 9 and lymph canal 13). The fatty areolar tissue is made of clusters of fat cells linked together by collagenous connective fibers. As used herein and in the claims, the term vascular tissue includes the vessel wall and any associated vascular sheath. It has been found that the vascular sheath 21, as explained more fully below, plays a role in properly closing the puncture site in the vessel wall 5.

Figure 10:
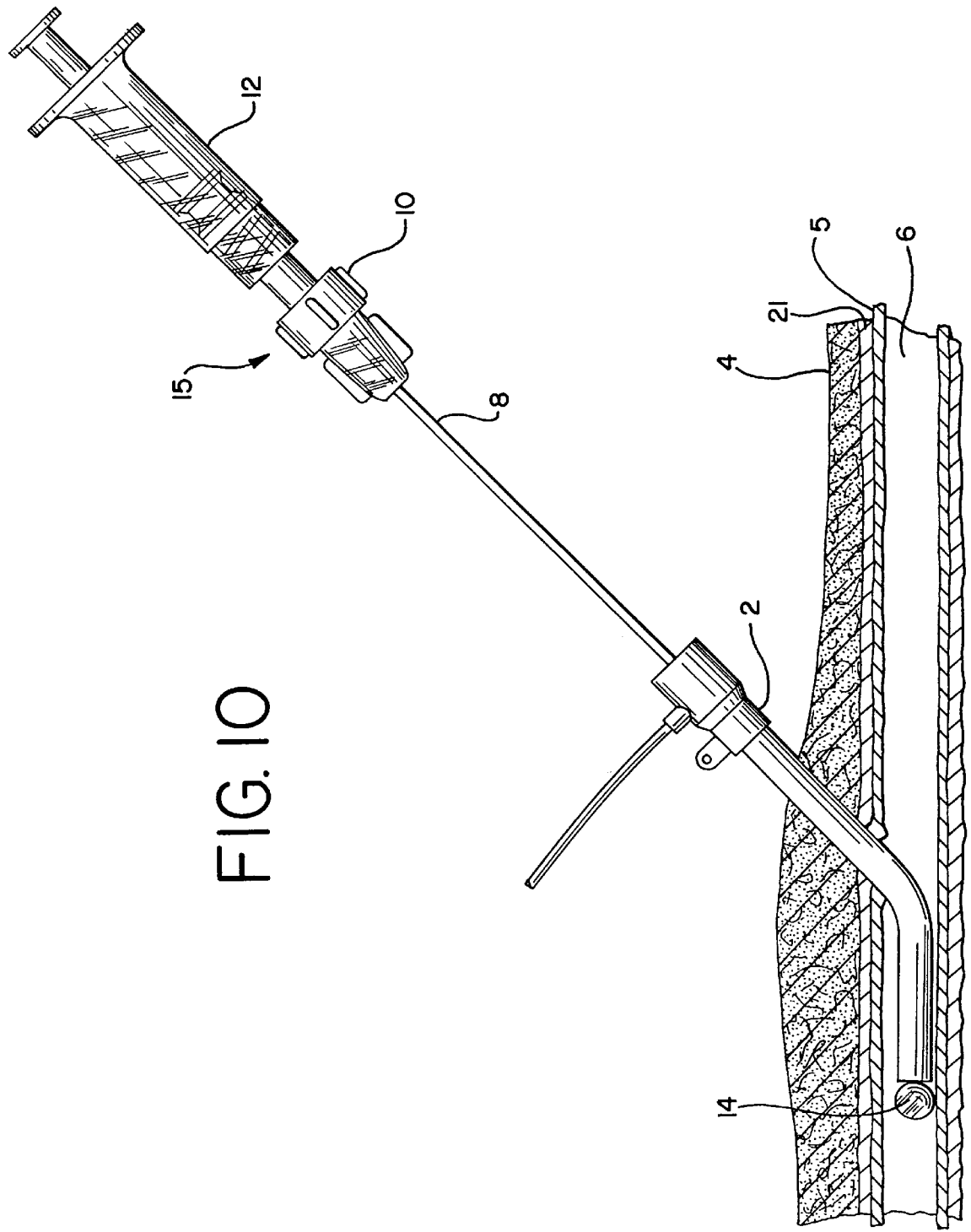

In use, a catheter introducer sheath 2, if not already in place from a prior medical procedure, is inserted into a vessel, such that it extends from the interior of the vessel lumen 6, through the vessel wall 5 and out through the vascular sheath 21, subcutaneous tissue 4 and skin surface of the patient (FIG. 9). The distal portion of the balloon occluder assembly 15 is inserted into the introducer sheath 2 through the diaphragm using the introducer (not shown), and pushed until the distal end of the balloon shaft 8 extends beyond the distal end of the introducer sheath 2 (FIG. 10).

The syringe 12 and the removable hub 10 are attached to the check valve assembly 20, and the balloon 14 is inflated with a predetermined volume of fluid, preferably saline. The balloon 14 is inflated to a size sufficient to occlude the puncture and preferably in the form of a sphere as shown, or more preferably in the form of a flat disk. Preferably, the syringe 12 is sized such that full displacement of its piston will provide the exact amount of fluid to properly inflate the balloon 14. The removable hub 10, together with the syringe 12, are then removed from the balloon occluder assembly 15. The check valve assembly 20 prevents deflation of the balloon.

The balloon 14 is withdrawn (i.e., pulled out of the body) until the inflated balloon abuts the distal end of the introducer sheath 2, and then both are withdrawn until the balloon abuts the puncture. At this point, the introducer sheath 2 is totally removed from the body, exposing the color bands or marking 24 on the balloon shaft 8 (FIG. 11). The balloon 14 temporarily occludes the puncture site to prevent bleeding. Digital pressure is thus not required.

The physician notes the markings 24 on the shaft 8 at the point where the shaft meets the surface of the skin (FIG. 11). The balloon occluder assembly 15, in addition to temporarily occluding the puncture, also functions (a) to identify for the physician the exact depth of the puncture, (b) to provide positioning support for the area surrounding the puncture so that the forceps 50 may more easily grasp the vascular tissue (i.e., a backstop element), (c) as a guide for a hemostatic device, including, but not limited to the cautery device 7 of the present invention and (d) to keep the vascular tissue through which the puncture has been made separated from the tissue of the opposite vessel wall. The importance of the various functions of the balloon occluder assembly 15 will become more evident as the subsequent steps in the preferred method are explained. It will be understood that backstop elements of additional preferred embodiments will also perform some or all of these functions.

The cautery sheath 30 and dilator 34 are inserted over the shaft 8 of the balloon occluder assembly 15 and into the skin. Based on the depth markings, the tapered distal end of the dilator 34 and cautery sheath 30 are inserted so that they do not penetrate the vessel, but merely abut it (FIG. 12). Once the cautery sheath 30 is in place, the dilator 34 is removed.

Referring to FIG. 13, the cautery device 7 is inserted over the shaft 8 of the balloon occluder assembly 15 and into the cautery sheath 30. As can be seen in FIG. 13, the check valve assembly 20, located at the proximal end of the shaft 8, is small enough in diameter to thread the cautery device 7 over it. The markings on the balloon shaft 8 and the cautery sheath 30 provide a means for placing the cautery device 7 at a predetermined distance from the puncture site.

The thumb rest 32 on the cautery device 7 is then depressed, causing the spring 28 to actuate the forceps 50 (FIG. 14). Upon actuation, the forceps 50 extend beyond the tubular retaining housing 38 and expand slightly due to the lack of radial compression provided by the retaining housing 38. The balloon occluder assembly is withdrawn slightly so as to bring the vascular tissue into proper position. The serrated gripping portion 52 of the forceps 50 grasps the vascular tissue surrounding the puncture at spaced points (FIG. 14). The balloon 14 provides, among other things, a backstop against which the vascular tissue is grasped. Referring to FIG. 15, the thumb rest 32 is released, causing the forceps 50 to retract or withdraw into the retaining housing 38, thus pulling the grasped tissue together until stopped by the balloon occluder assembly 15.

As shown in detail in FIG. 15A, the vessel wall 5 is made of three layers. The innermost layer is the intima 16, which is the most delicate and important layer for vessel health and healing. It is preferred that any heat conducted to or generated in the vessel wall be limited to the other layers so that the intima layer is not substantially heated so as to preserve the cells in the intima layer. The second layer is the media 17. The media is dense and will resist being pulled by the forceps 50. The outer layer is the adventitia 18. The adventitia is fibrous and somewhat loose. It is easier to grasp and is more flexible and elastic than the other layers. If the forceps 50 anchor in the adventitia layer 18, the adventitia can be pulled closed without drawing the media layer 17 together.

Figure 16:
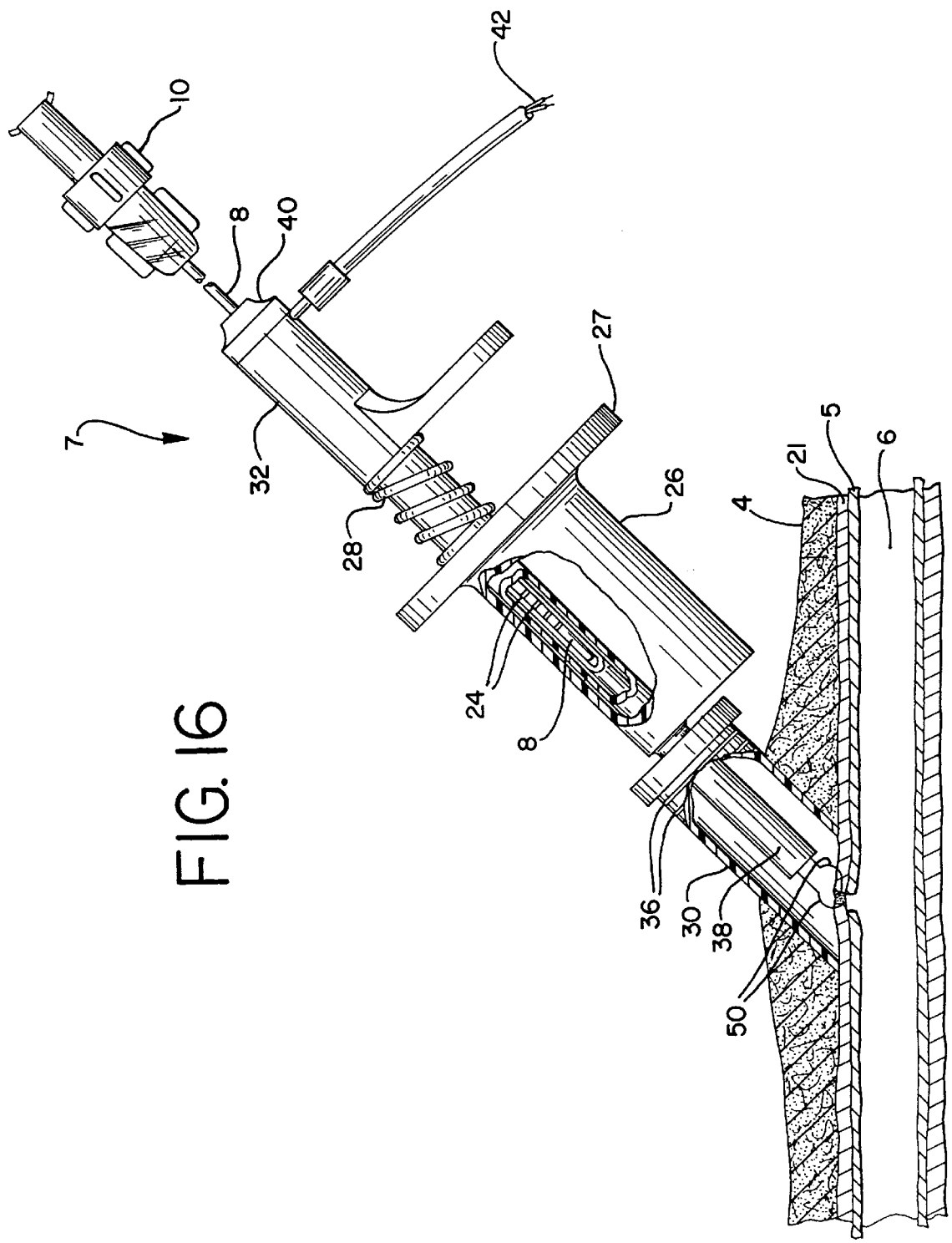

Preferably the forceps 50 penetrate through the vascular sheath 21 and anchor in the adventitia layer 18 as shown in FIG. 15A. The balloon 14 is then deflated by putting the hub 10 back onto the end of the check valve assembly 20 (FIG. 16). The deflated balloon passes through the grasped tissue. The entire balloon occluder assembly 15 is fully withdrawn from the cautery device 7. The forceps 50 continue to grasp the tissue, pulling the vascular sheath 21 and adventitia layer 18 surrounding the puncture together (FIG. 16).

The radio frequency power supply (not shown) is then activated and the electrodes are energized. In the first preferred method, a thumb or foot switch is used to activate the power. The tissue in between the forceps 50, which serve as electrodes, acts as a high resistance conductor. It will be understood that the parameters of the electrical energy applied to the vascular tissue surrounding the puncture site must be selected to thermally fuse the puncture without causing widespread damage to the tissue or coagulating blood in the vessel. The frequency of the alternating electrical energy can be anywhere in the radio frequency range (10 kHz to 300 GHz). For medical reasons, the frequency should be above 25 kHz. For most applications, a high frequency energy range, generally 300 kHz to 1,000 kHz, may be used, with the frequency preferably being in the range of 300 kHz to 600 kHz, more preferably between 450 kHz and 550 kHz, and most preferably 500 kHz. In other applications, frequencies in the short wave range (10 MHz to 100 MHz), or in the microwave range (1 GHz to 300 GHz), will be more useful. A duration of application of the energy will generally be between about one and ten seconds.

It has been found preferable to start the cauterization procedure before the forceps 50 get too close to one another to prevent shorting out between them. In fact, it may be preferable to energize the electrodes while the balloon occluder assembly 15 is still between the forceps 50. The vascular tissue is instantaneously heated as the current passes from one electrode to the other. It is believed that the generated heat denatures or melts the collagen in the tissue, causing the tissue to fuse together and close the puncture. In addition, the heat generated may cause thrombosis or coagulation of blood which seals the puncture. After the vascular tissue has been thermally fused, the electrodes are deenergized.

FIG. 17A shows in detail how a puncture may be sealed if the forceps 50 are anchored as shown in FIG. 15A. The tissue from the femoral sheath 21 and adventitia 18 is drawn together and fused. The fused tissue forms a cap or plug over the puncture. The plug may include a weld 19 of the sheath 21 as well as a weld 29 of the adventitia layer 18, or the cap may be a homogenous mass of fused collagen. The gap between the media layers 17 is quickly closed with an arterial clot, and the intima layer 16 starts to grow closed a short time later.

If the forceps 50 only grasp the arterial sheath 21, it is possible that a cap or weld 19 of the sheath will only occur in the sheath, but that a plug will form below the sheath 21 and above the opening in the vessel wall to seal the puncture. Also, even though current may flow only between grasped portions of sheath 21, heat generated thereby may be conducted to the vessel wall 5 to also heat and fuse the adventitia layer 18.

Figure 18:
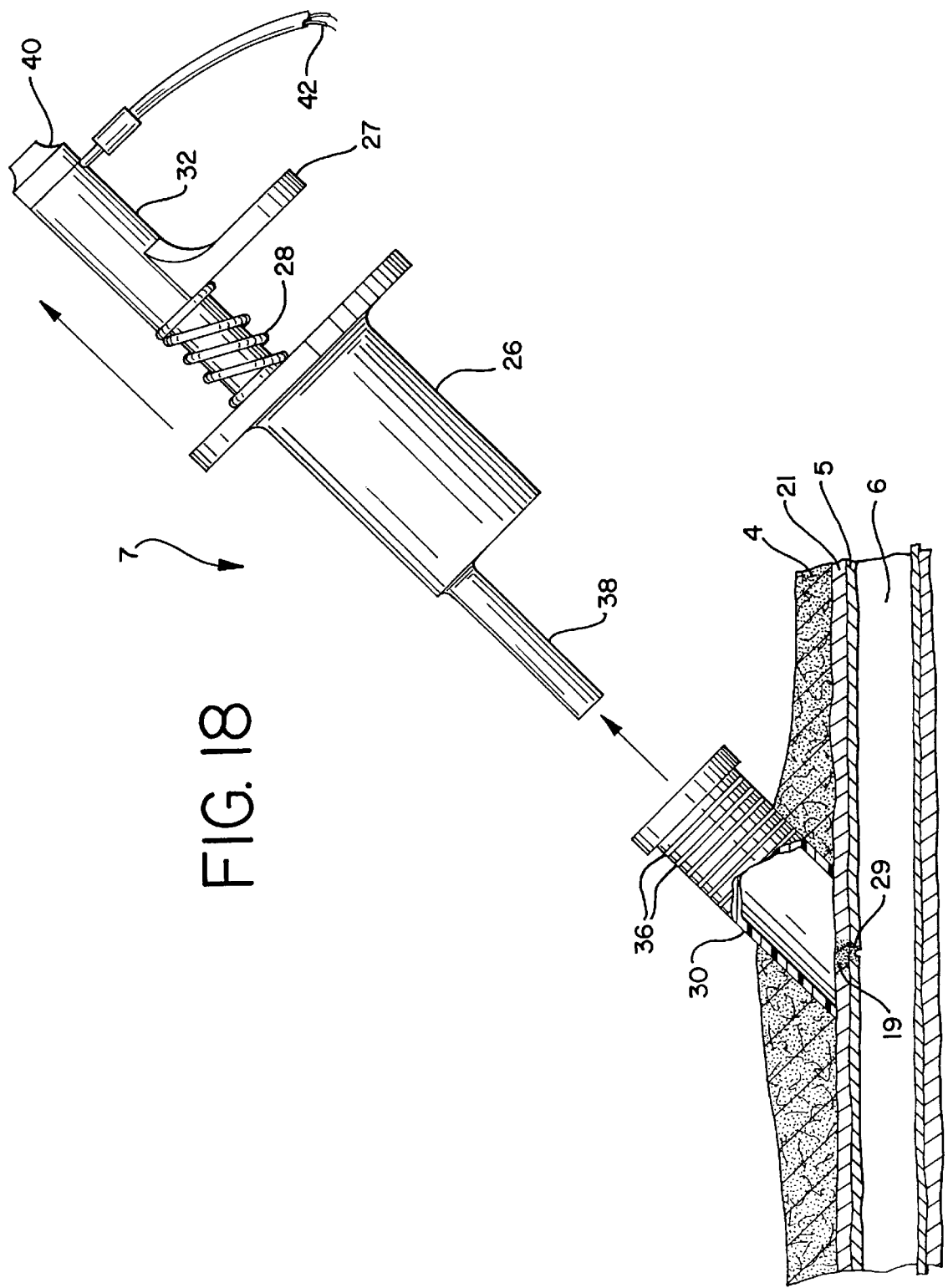

After the seal has been formed, the thumb rest 32 is depressed once again, causing the forceps 50 to expand slightly, thus releasing the vascular tissue (FIG. 17). The cautery device 7, followed by the cautery sheath 30, are removed from the body, leaving the vascular puncture hemostatically sealed (FIG. 18).

Additional preferred embodiments of the actuator element of the cautery device 7 are shown in FIGS. 6–8. FIG. 6 illustrates a cautery device 107 comprising a gripping handle 126, which pivots about a screw, causing a portion of the gripping handle to compress a spring and actuate the forceps 50. Similarly, FIG. 7 illustrates an additional preferred embodiment of the cautery device 207 comprising a rack and pinion mechanism 226 for actuating or moving the forceps 50 from a first position to a second position. FIG. 8 shows another preferred embodiment of the cautery device 307 wherein the gripping handle comprises a wedge which acts against an inclined plane 326 and compresses a spring when squeezed, actuating the forceps 50. Also contemplated by this invention are cautery devices comprising additional suitable mechanisms for actuating the forceps 50.

In addition to the balloon occluder assembly of the first preferred embodiment, the present invention contemplates the use of any other device, assembly or mechanism which will provide a backstop for the tissue surrounding the vascular puncture. The backstop element, the distal portion of which is located inside the puncture, essentially functions as an anchor or a positioning mechanism to provide positioning support and to help guide a hemostatic device to the puncture site, both laterally and longitudinally (depthwise).

In an additional preferred embodiment, the backstop element is a T-shaped occluder 114 adapted to be inserted into the vessel lumen 6 to provide positioning support for the tissue surrounding the vascular puncture and to temporarily occlude the puncture (FIGS. 19A & 19B). The purpose of providing positioning support to the tissue surrounding the vascular puncture is to allow the forceps to more easily grasp the vascular tissue and to grasp only the proper tissue, i.e., to prevent the cautery forceps from grasping and sealing the entire vessel. The purpose of temporarily occluding the puncture is obviously to prevent blood or fluid loss.

The backstop element may be connected to a guiding shaft, such as the guiding shaft 108 as shown in FIGS. 19A & 19B. The guiding shaft 108, similar to the balloon shaft 8, allows the backstop element to be manipulated and controlled from outside the body and also provides a means for determining the depth of the puncture.

The T-shaped occluder 114 is made of a flexible, springy material. It may be either plastic pre-bent into a T shape or a coiled wire similar to that of conventional guide wires. The T-shaped occluder may have more horizontally extending legs than just the two shown. Prior to insertion (FIG. 19A), the T-shaped occluder is disposed in the guiding shaft 108 similar to the balloon shaft 8 of the first preferred embodiment. The radial compression of the guiding shaft 108 causes the horizontal portion of the T-shaped occluder to fold up. The folded-up horizontal portion forms the distal end of the T-shaped occluder. In use, the distal end of the occluder is pushed out of the guiding shaft 108, causing the folded-up portion to unfold and contact the interior surface of the vessel wall immediately proximate the puncture (FIG. 19B). The perpendicular vertical portion of the occluder extends out from the vessel lumen 6 through the puncture, into the guiding shaft 108 and to the skin surface. A spring 112 is used to move the T-shaped occluder from a first position to a second position. A locking mechanism 120, particularly a locking pin 122, is used to keep the T-shaped occluder in its first or second position.

Although it is preferable to use a backstop element which functions to provide positioning support and to temporarily occlude the puncture, it is not necessary. That is, another aspect of the present invention provides a method of sealing a vascular puncture wherein the introducer sheath is withdrawn from the vascular puncture, a cautery sheath is inserted and the distal end of the cautery device is then inserted into the cautery sheath and activated as previously described. If no backstop element is used, however, digital pressure may be required to temporarily stop the bleeding from the puncture.

An additional preferred embodiment of the present invention contemplates the use of an internal plunger mechanism as a means for inflating the balloon 14. The internal plunger mechanism would fit within the shaft 8 and would use the air already present in the shaft to inflate the balloon. The mechanism would incorporate a check valve to keep the balloon inflated and would thus alleviate the need for the removable hub 10, syringe 12 and check valve assembly 20 which comprise the inflation means of the first preferred embodiment.

The present invention incorporates an assembly for temporarily occluding a vascular puncture, as discussed above, which, when used with a hemostatic device or composition, effectively and efficiently seals a vascular or other percutaneous puncture. Additional aspects of the present invention include the use of any suitable hemostatic device or composition known in the art in conjunction with the occluding assembly mentioned above. Although the preferred hemostatic means of the present invention is the cautery device 7, additional devices or compositions which are capable of hemostatically sealing a vascular puncture, such as a tissue adhesive, a thrombotic agent, a vascular clip, sutures or a suturing device, are contemplated for use with the occluder assembly.

Another aspect of the present invention is to provide an assembly adapted to guide a hemostatic means to a puncture site. The first preferred embodiment disclosed the use of a balloon occluder assembly. Any assembly, however, comprising an elongated shaft having a positioning mechanism at the distal end thereof and a means for controlling or manipulating the positioning mechanism at the proximal end thereof, wherein the distal end of the elongated shaft is insertable into the lumen of a vessel and the positioning mechanism is configured to anchor the distal end of the assembly inside the vessel, is contemplated. Any such assembly should further prevent entry of the hemostatic means into the vessel through the puncture site. Preferred embodiments of such an assembly include the balloon occluder assembly and the T-shaped occluder device.

Another aspect of the present invention is to provide an assembly adapted to determine the depth of a percutaneous vascular puncture. One embodiment thereof comprises an elongated member having markings thereon and a positioning mechanism at the distal end thereof, as previously described. Any such assembly adapted to measure the depth of a percutaneous vascular puncture from the level of the skin when the distal end of the elongated shaft is inserted into the lumen of the vessel is acceptable.

An additional aspect of the present invention is to provide a method of sealing a vascular puncture which does not require the use of a cautery sheath or dilator. Instead, the original introducer sheath may be used in place of the cautery sheath if it is withdrawn slightly from the puncture site so that it is not in the vessel lumen 6.

In additional preferred embodiments, the means for forcing together biological tissue may include any conventional system or mechanism suitable for pulling, pushing or causing tissue to come together. In addition to forceps, one such means may be a vacuum system. In a vacuum system, the force of the suction causes the vascular tissue to be pulled into a contacting position. Other mechanical systems which push the tissue together may also be used.

In some methods of the invention, the tissue may not need to be grasped, or at least not pulled all the way together. It has been found that as heat is generated in, or thermally conducted to, the tissue surrounding the puncture, the tissue undergoes a sphinctering effect, closing upon itself to seal the artery. Depending on the size of the puncture, a radio frequency cautery device could be percutaneously inserted such that its electrode or electrodes are proximate the puncture site and then the radio frequency energy would cause this sphinctering effect and coagulation of the blood to seal the opening. In this method, pressure would be applied to the vessel to restrict blood flow therethrough while the cauterization was performed. Alternatively, the cautery device could include a through-lumen, as described below in conjunction with FIGS. 20–23, and blood flow through the lumen could be monitored during the sealing process, cessation of flowing blood being indicative of completion of the sealing process.

Bipolar electrodes are preferred, although monopolar electrodes are also contemplated by the present invention. One of the prongs of the forceps 50 may thus comprise a monopolar electrode, or a separate monopolar electrode may be located proximate to the forceps, such that radio frequency energy can be applied to the biological tissue which is held in a contacting position by the forceps. Alternately, a monopolar electrode may be placed in the center of the forceps 50, or used without the forceps 50 where the tissue can be treated without being grasped. When a monopolar electrode is used, the patient is grounded using a grounding pad. Most of the electrical energy is concentrated, and most of the heat generation occurs, in the tissue contacting the electrode. However, energy is transmitted to deeper layers (such as through the arterial sheath 21 and into the vessel wall 5) as the current dissipates and moves toward the grounding pad, and this current then produces heating at the sites near the electrode where the current density is highest.

Since the use of heat is the operative element in the process, the invention also contemplates delivering heat to the tissue by thermal conduction from a heated probe, as discussed below in conjunction with FIG. 24. Thus the energy that is directly conducted to the tissue may be electrical energy (either alternating current or direct current, including pulsed direct current) or thermal energy. Microwave energy may also be used to generate heat in the tissue, particularly if a probe is constructed with a microwave source or receptor at its operative tip.

Depending on how the heat is conducted to or generated in the tissue, and whether the tissue is grasped together, the heat will fuse the tissue in a variety of mechanisms, including fusing, coagulation of blood and combinations thereof.

Additional embodiments of probes that can be used to seal vascular punctures are disclosed in FIGS. 20–24 and 31–32. These devices do not include forceps that grasp the tissue, but instead use monopolar and bipolar electrodes or a heated probe tip to directly contact the tissue and affect a seal.

FIG. 20 shows a probe 130 that has a monopolar electrode 132 connected to a power supply 134. The power supply is also connected to a grounding plate 136. The grounding plate 136 is in electrical contact with the patient during the vascular sealing procedure. The grounding plate or pad is of a greater cross-sectional area than the probe so that the current density at the grounding pad is much less than at the probe tip, to prevent burning the patient's skin.

The probe 130 has an insulating covering 133 over the electrode 132 except at the distal tip 131 of the probe 130. The exposed portion of electrode 132 may thus conduct electrical energy to the vascular tissue, such as the vascular sheath 21 or vessel wall 5. The probe's small surface area and the high resistance contact with biological tissue results in areas of high current density causing localized heating of the vessel and/or adjacent tissue.

The probe 130 is designed as a "monorail" probe so that it can be guided to the site of the vascular puncture by a guide wire 139 that is in the vessel lumen 6. The guide wire 139 may be metal or a nonconducting material such as plastic. A hole 138 extends through the center face of the exposed electrode 132 at the tip 131 of the probe 130 and extends out of the side of the probe 130 at a point that is outside of the patient's body when the probe is inserted to a depth where it contacts the vessel wall 5. The inside of probe 130 contains insulation 135, and the hole 138 is also preferably provided with an insulation layer 137 (best seen in FIG. 20A) that prevents the guide wire 139 from contacting electrode 132.

To use the probe 130, it is threaded over the guide wire 139, which acts as a guiding element, and percutaneously inserted through the tissue 4 until it comes in contact with the arterial sheath 21 and/or vessel wall 5. The guide wire 139 can then be removed and the power supply 134 activated to provide electrical energy to electrode tip 131. The energy dissipates through the tissue, generating heat therein to seal the opening. In this embodiment, blood will flow out of the hole 138 until the puncture is sealed. Hence, completion of sealing will be evident by cessation of blood flow from hole 138. This also has the advantage that blood is conducted away from the sealing area, which prevents pooling in the area and reduces scar tissue. Alternatively, the guide wire 139 can be withdrawn as energy is being applied.

The probe 140 of FIG. 21 is very similar to the probe 130 of FIG. 20, except that the hole 148 for guiding the probe 140 extends in an "over-the-wire" fashion through the center of the probe 140. Also, the electrode 142 ends in an exposed tip 141 that has an annular shape, like the cross-section of the electrode 132 seen in FIG. 21A. Insulating layer 143 on the outside of the electrode 142 isolates the electrode 142 from contact with the patient except at the tip 141. The probe 140 also has an insulation layer 145 on the inside isolating hole 148 from electrode 142. The probe 140 is used in the same fashion as described previously for probe 130, with power supply 144 and grounding plate 146.

FIGS. 22 and 23 show bipolar electrode probes 150 and 160. In a bipolar arrangement, no grounding pad is needed. The probes 150 and 160 each have two electrical leads connected to the power supply 154 and 164 respectively and two electrodes. Probes 150 and 160 each include holes 158 and 168 respectively, that allow guiding the probes to the puncture site, as well as insulating layers 153, 163, 165 and 167 similar to the insulation in probes 130 and 140. In probe 150, the two electrodes 152A and 152B are both arcuate in shape, and are located opposite of hole 158 from each other, as shown in FIG. 22A. In probe 160, the two electrodes 162A and 162B are concentric, as best seen in FIG. 23A. In both probes, the exposed tips 151 and 161 provide two electrodes that contact the tissue at spaced points from one another. Thus the operation of these electrodes in contact with the tissue is similar to the operation of forceps 50 in FIG. 16.

FIGS. 31 and 32 show an electrocautery device 300 and an elongated probe 310 that can be used to seal a vascular puncture. The probe 310 is bipolar, but in this design, its two electrodes have quite different shapes, and contact different types of tissue. The distal tip of the first electrode 312 is a half sphere and forms the distal tip of the probe 310. In use, the distal tip of electrode 312 is placed at the site of the puncture in arterial wall 5 and vascular sheath 21. The other electrode 316 is a hollow, elongated cylinder, a portion of the outside surface of which contacts the subcutaneous tissue 4. A piece of insulation 313 separates the electrodes 312 and 316, and covers up all but the distal tip of electrode 312.

The electrocautery device 300 designed for use with the probe tip 310 comprises a body 302, configured as a handle for the device, and a thumb activated momentary switch 304. Wires 305, 306 and 307 from the power supply (not shown) enter the body 302 of the electrocautery device 300 at its proximal end. The wires 305, 306 and 307 are preferably insulated in the form of a cord 308 outside of the body 302. Wire 306 terminates in a contact point 301 inside the body 302. Wire 307 connects to a contact point 303.

When the probe tip 310 is inserted into the body 302 of electrocautery device 300, contact point 301 forms an electrical contact with electrode 312, and contact point 303 forms an electrical contact with electrode 316.

Wire 305 is used to make the switch 304 a momentary switch. When switch 304 is activated, the circuit between wires 305 and 307 is closed. This circuit then activates a timing circuit in the power supply, and the power supply provides bipolar current to the electrodes 312 and 316 for a predetermined period of time.

The relatively large contact space between electrode 316 and the subcutaneous fatty tissue 4 and associated fluids provides an adequate electrical contact to avoid localized cauterization adjacent electrode 316. The small contact surface of the distal tip of electrode 312, on the other hand, concentrates electrical current in the vicinity of the puncture in arterial wall 5, thus causing an electrocautery sealing of the vascular puncture.

The body 302 and probe tip 310 each include a lumen 309 and 319 respectively for use in guiding the probe 310 to the puncture. As shown in FIG. 32, the electrocautery device 300 is an "over-the-wire" configuration, but it could also be designed to have a "monorail" configuration.

When using the cautery devices of FIGS. 20–23 and 31–32, a preferred power supply is either the Radionics CVC-1 or Valley Labs SSE2-K RF power generator. These power supplies may also be used with the cautery device of FIG. 16. The voltage applied to the cautery devices will generally be in the range of 25–200 volts (RMS), with 40–80 volts (RMS) being preferred, and 60 volts (RMS) being most preferred. The electrodes may be stainless steel.

The probe 170 of FIG. 24 provides thermal energy, rather than electrical energy, to the tissue to seal the vascular puncture. The probe 170 includes an insulating handle portion 173 with two wires 172 contained therein. The wires 172 connect to an appropriate power supply 174, that may be different than the power supply used for the probes 130, 140, 150 and 160. Inside the tip 171 of probe 170 the wires 172 connect to a heating element 175. When current from the power supply 174 is conducted through wires 172, heating element 175 will heat tip 171 of probe 170. This heat will then be thermally conducted to tissue in contact with the tip a 171. The tip 171 is preferably made of metal or any other good heat conducting material, and is preferably coated with a non-stick coating, 179, such as TEFLON®. The shape of the tip 171 may be configured to provide heat to a specific area desired for sealing the vascular opening. The probe 170 can also be provided with a hole through it if desired for purpose of guiding the probe.

FIGS. 25–30 depict additional embodiments of depth finding and guiding devices that may be used in conjunction with the cautery devices disclosed herein, or other techniques for sealing vascular punctures. FIG. 25 shows an apparatus that includes an elongated member 182, a dilating member 186 and a cautery sheath 189. The elongated member 182 has a lumen 183 inside of it and a port 184 in the side, the port 184 extending into and thus being in fluid communication with the lumen 183. The lumen 183 has an exit opening proximal of the port 184. In a preferred embodiment, the lumen 183 opens at the proximal end of the elongated member 182, which is threaded for attachment to the distal end of dilating member 186. In this embodiment, the port 184 is located near the proximal end of the elongated member 182 so that when the elongated member 182 is attached to dilating member 186, the port 184 is spaced from the distal end of dilating member 186 at a distance about equal to the thickness of the arterial sheath 21 and vessel wall 5 (FIG. 26).

In addition to having a threaded opening 187 to accept the threaded end of elongated member 182, dilating member 186 also has a lumen 188 through it. The cautery sheath 189 is sized to slide snugly over the outside of dilating member 186, and is preferably tapered at its distal end. The cautery sheath 189 serves the same function as cautery sheath 30 as shown in FIG. 12, to spread the subcutaneous tissue above the vascular puncture to provide a work area for cauterization. The dilating member 186 and cautery sheath 189 will thus preferably be sized at least as large as the cautery device that is to be used with the apparatus of FIGS. 25–27.

The elongated member 182 is preferably inserted into the vessel lumen 6 through an introducer sheath 2 left in place after a prior medical procedure, similar to the way that balloon occluder assembly 15 is inserted (FIG. 9). Thereafter the introducer sheath can be removed. The elongated member 182 is preferably sized so that the puncture in the vessel wall 5 will be able to close around it when the introducer sheath is removed. After the introducer sheath is removed, the dilating member 186 is attached (screwed on) to the elongated member 182 and the combined unit is inserted further into the vessel lumen. At the point at which port 184 passes the vessel wall 5, which is preferably at the same time that the distal end of dilating member 186 abuts the outside of the vessel wall 5 (or the arterial sheath 21) blood will enter the port 184 and flow through lumen 183, through lumen 188 and out the end of dilating member 186. The depth of the vascular puncture from the surface of the skin can then be noted.

Next, the cautery sheath 189 is slid over the dilating member 186 and forced downwardly until it also contacts the outside of the arterial sheath 21 or vessel wall 5. Preferably a mark 191 on the dilating member 186 will be used to show how far the cautery sheath 189 needs to be inserted. While holding the cautery sheath 189 in place, the dilating member 186 is withdrawn until it can be detached from elongated member 182, which still extends into the vessel and is occluding blood flow (FIG. 27). The cautery sheath 189 is left, spreading the subcutaneous tissue superficial to the surface of the vessel wall to an opening dimension that is larger than the opening in the vessel wall. The elongated member 182 then acts as a guiding element and can be used to guide a probe, such as probe 130, 140, 150, 160 or 310, to the puncture site. The probe can be marked so that when it slides into the cautery sheath 189 to the proper depth, the mark will align with the top edge of cautery sheath 189. The elongated member 182 may thereafter be removed from the vessel, or removed as the probe is activated, as previously described.

The benefit of this apparatus is that the probe tip is provided clear access to the vessel wall 5 to seal the puncture. When the probe tip is shaped to dilate the tissue as it is inserted, as probe 130 in FIG. 20 or probe 310 in FIG. 31, it may not be necessary to use the cautery sheath 189 and dilating member 186. Instead, as shown in FIG. 28, the cautery probe 293 is used only with the elongated member 282, which in this embodiment has the port 284 located much closer to the distal end of the elongated member 282. In the embodiment of FIG. 28, the elongated member 282 is inserted into the vessel over a guide wire 295. Alternatively, the elongated member 282 can be inserted through an introducer sheath as with elongated member 182, in which case no guide wire is needed and the distal tip of elongated member 282 is closed. In either embodiment, the elongated member 282 is inserted until the depth of the vessel is determined, evidenced by blood flowing out the end of lumen 283.

The cautery probe 293 is then threaded over the elongated member 282 and forced downwardly until it engages the arterial sheath 21 and/or vessel wall 5. Preferably, a mark 291 or other indicia on the elongated member 282, specific for the length of the probe contemplated for use, will be visible at the top of the probe 293 when the port 284 is just inside of the vessel 6 and the distal end of the probe 293 abuts the outside of the artery wall 5. In one alternative embodiment, another side port could be placed in the elongated member at the location of mark 291. This port could serve both as the exit for the blood flow out of the lumen, as well as an indicia used as a depth reference point.

After the proper depth has been determined and the probe is in place, the guide wire 295 and elongated member 282 can be removed and the probe activated. Alternatively, the probe can be activated while the guide wire 295 remains in the vessel 6. When the guide wire 295 is later removed, there will be either a small hole, which will quickly clot closed, or the vessel wall 5 will further contract to seal the hole left by the guide wire 295. Alternatively, further sealing may be achieved after removal of the guide wire 295 by another discharge from the cautery probe. In embodiments of the invention where the probe is activated while the guide wire 295 is in the artery, the guide wire 295 should either be made from a non-conductive material, or be electrically insulated from the electrodes, to prevent electrical energy from being transferred to the guide wire 295 and the blood and vessel wall 5 distant from the puncture site.

The use of guide wire 295 in FIG. 28 is beneficial because the elongated member 282 may be fairly stiff, and the guide wire therefore eases the entry of the elongated member 282 into vessel lumen 6. The guide wire 295 can be one that is already in place, or can be inserted with the elongated member 282.

When using the guide wire 295, the elongated member 282 must have an opening at its distal end to allow the guide wire to be inserted through it. In those embodiments, it is preferable for the lumen 283 of the elongated member 282 and the guide wire 295 to be sized to seal this opening so that blood does not enter the lumen 283 until the port 284 enters the vessel lumen 6. The embodiments of FIGS. 29 and 30 show two different alternatives to achieve this sealing. In the alternative of FIG. 29, the guide wire 295' has an enlarged section 296 at its distal end which is larger in cross-section than the distal end of lumen 283. Thus guide wire 295' can be pulled into lumen 283 to seal it. In the embodiment of FIG. 30, the lumen 283' has a cross-section larger than the diameter of the guide wire from at least the point where it communicates with port 284 to the proximal end of the lumen 283', and a smaller cross-section at the distal end of the lumen 283'.

The elongated member 182 or 282 may be formed of a number of materials including metals, such as stainless steel, copper or silver, or plastics, such as polyethylene, polyester, polytetraethylenefluoride or nylon. The lumen 183 need not be concentric in the elongated member 182, and there may be more than one lumen in fluid communication with different ports.

The elongated member 182 will generally be 8 to 36 inches in length, and preferably 12 to 24 inches long. The outside diameter of the elongated member 182 will be in the same range as the inside diameter of commonly used introducer sheaths. For an 8 French sheath, the outside diameter of elongated member 182 will be about 0.104 inches. The diameter of the lumen 183 will generally be up to 0.1 inches, and will preferably be between 0.005 and 0.02 inches. The size of port 184 will generally be up to 75% of the outside diameter of the elongated member 182, and preferably between 0.001 and 0.01 inches. The port can be situated anywhere along the length of the tube, but will preferably be between 2 to 4 inches from the proximal or distal tip for the embodiment of FIG. 28. There are preferably markings from the port 184 to the proximal end of the elongated member 182 to indicate the distance to the port, and hence the depth of the vessel wall 5. The dilating member 186 may also have more markings than mark 191. The dilating member 186 will generally be 4–8 French sizes larger than the puncture size. The cautery sheath 189 will have a slightly larger inside diameter than the outside diameter of dilating member 186. The cautery sheath will generally be 2 to 8 inches in length, more preferably 3 to 4 inches long.

The probes 130, 140, 150, 160 and 310 will preferably be 2 to 6 French sizes larger in outside diameter than the elongated member 182, and of course have an inside diameter that just fits over the elongated member 182. For example, if the elongated member 182 is 8 French, the probe will preferably have an 8 French internal diameter guiding hole and be 10 to 16 French in outside diameter.

In some instances it may be helpful to use ultrasound to verify the position of the guiding devices or electrocautery probes described above. For example, the SiteRite™ compact ultrasound system from Dymax Corporation, 604 Epsilon Drive, Pittsburgh, Pa. 15238 has been used to help guide internal jugular vein cannulations, and could be used in a similar fashion to verify the spatial relationship (depth and position) of the probe tip and the arterial puncture. FIG. 33 shows the cautery device 300 being used to seal a puncture in artery 6. The position of the probe 310 can be verified by viewing images resulting from the ultrasound system 320. The portion of the arterial wall 5 and subcutaneous tissue 4 visible in the ultrasound image is shown by dashed line 321.

Another method of determining the depth of the arterial wall is to outfit a probe with a Doppler flow detection system, such as that used in the SmartNeedle™ vascular access device sold by the Peripheral Systems Group, An ACS® Company, 1395 Charleston Road, Mountain View, Calif. 94043. Alternatively, the Doppler flow detection system may be placed on a separate guiding element, similar to elongated member 282, which is used to locate the depth of the arterial wall, followed by guiding the electrocautery probe to the vascular puncture using this guiding element.

Other techniques and apparatus may be used to determine the depth of a vessel wall and to otherwise aid in wound closure processes. One such device is a flow anemometer, which comprises two thin coils of wire spaced slightly apart on a probe and heated by passing electrical current therethrough, causing resistance heating. By constructing the coils out of wire with a temperature-dependent resistance, the position of the probe with respect to the vessel can be determined by comparing the resistance between the two coils, because blood flow past a coil within the artery will reduce its temperature, and hence its resistance, compared to a coil outside of the artery.

Another useful device is a tube with longitudinal slits on the distal end and a shaft through the tube with a balloon or other object on the distal end of the shaft. The device is inserted into the artery just as the balloon or T-shaped occluder described above, and the shaft withdrawn from the tube until the small balloon engages the distal end of the tube, causing the slit portions of the tube to expand radially. In this position, the slit portions can serve as a backstop element, and markings on the tube can be used to determine the depth of the arterial wall.

Another device, similar to the T-shaped occluder, comprises a tube with a plurality of flaps formed by making longitudinal slits in the side of the tube. A non-kinking wire, such as nitinol or Elgiloy™, attaches to the inside of each flap and passes out the proximal end of the tube. When the end of the tube and the flaps are inside the artery, the wires are pushed to cause the flaps to open outwardly.

Yet another device comprises wires that form a collapsed cage at the distal end of the device. When the end of the device is in place within the artery, the wire cage is activated to open, such as by drawing the end of the device connected to one end of the wires towards a stationary portion of the device connected to the opposite end of the wires. The wires in the expanded configuration make up a cage that is larger than the vascular puncture, providing a backstop and positioning element. The cage is collapsed and withdrawn after it has served its function. If desired, the wire cage could be covered with an elastomeric material, such as latex rubber, Kraton or silicon rubber, to make it more like the balloon occluder.

Another device includes a strip of thin material wound into a flat coil like film on a reel. One end of the strip is connected to an outside tube and the other end is connected to a rotatable shaft inside of the outside tube. Once the coil is within the artery, turning of one tube relative to the other causes the coil to unwind and expand the diameter of the flat coil. In its expanded state, it can serve as a backstop, positioning and depth-finding device, then rewound to a tight coil for removal.

Yet another device includes three plate-like elements stacked on top of each other and connected near their outside edges by pivot points such that two of the plates can pivot outwardly from opposite sides of the third plate so that the plates are next to each other in a line. The device includes shafts to actuate these pivot points. Once the plates, stacked on top of each other at the distal ends of the shafts, are in place in the vessel, the shafts are rotated so that the plates spread out, thus providing a backstop, positioning and depth-finding element within the vessel.

One additional device includes a lumen connected to a port, but does not allow for the use of a guide wire. Instead, in this device the blood is prevented from passing out of the lumen. A piston within the lumen is moved upwardly by blood pressure when the port enters the vessel lumen, until the piston reaches a stop position. The top portion of the piston then extends out of the proximal end of the device, or is otherwise visible, indicating that the port has entered the artery. The port can be in either the side of the device, or its distal end can be open to provide the port.

It should be appreciated that the apparatus and methods of the present invention are capable of being incorporated in the form of a variety of embodiments, only a few of which have been illustrated and described above. The invention may be embodied in other forms without departing from its spirit or essential characteristics. For example, the guiding and occluding aspects of the invention can be used with other vascular sealing systems. The described embodiments are to be considered in all respects only as illustrative and not restrictive, and the scope of the invention is, therefore, indicated by all the appended claims rather than by the foregoing description. All changes which come within the meaning and range of equivalency of the claims are to be embraced within their scope.

We claim:

1. An apparatus for percutaneously sealing a vascular puncture, said apparatus comprising:
   a) an elongated member having a lumen therein and at least two electrodes connectable to a radio frequency power source, said electrodes being adapted to contact biological tissue at spaced points; and
   b) said lumen being adapted to guide the electrodes to the biological tissue at said spaced points, said apparatus being adapted to thermally fuse together biological tissue surrounding said vascular puncture to effect closure thereof.

2. The apparatus of claim 1 wherein the two electrodes are concentric with one another and concentric with said lumen.

3. The apparatus of claim 1 wherein the elongated member comprises an elongated probe having a distal tip and a side surface, the first electrode forming the distal tip of the probe and the second electrode forming at least a portion of the side surface.

4. A method of using radio frequency energy to close a vascular puncture comprising the steps of:
   a) guiding a cautery device to the site of the vascular puncture, said cautery device comprising at least one electrode connected to a radio frequency energy source; and
   b) activating the radio frequency energy source, thereby causing the tissue surrounding the puncture to fuse together.

5. The method of claim 4 wherein the cautery device includes a lumen therein and is guided to the site of the vascular puncture by passing the lumen over a guiding element extending from the vascular puncture.

6. The method of claim 5 wherein the cautery device is guided to the vascular puncture using a Doppler flow detection system.

7. The method of claim 6 wherein the step of guiding the cautery device to the vascular puncture comprises using ultrasound to guide the cautery device to the site of the vascular puncture.

8. A method of using radio frequency energy to close a vascular puncture comprising the steps of:
   a) guiding a cautery device to the site of the vascular puncture using a Doppler flow detection system, said cautery device comprising at least one electrode connected to a radio frequency energy source; and
   b) activating the radio frequency energy source, thereby causing the tissue surrounding the puncture to fuse together.

9. The method of claim 8 wherein the cautery device has a distal portion and is equipped with the Doppler flow detection system on said distal portion.

10. The method of claim 8 wherein a guiding element equipped with a Doppler flow detection system is first guided to the vascular puncture aided by the Doppler flow detection system and the cautery device is guided to the site of the vascular puncture using said guiding element.

11. A method of using radio frequency energy to close a vascular puncture comprising the steps of:
    a) guiding a cautery device to the site of the vascular puncture using ultrasound, said cautery device comprising at least one electrode connected to a radio frequency energy source; and
    b) activating the radio frequency energy source, thereby causing the tissue surrounding the puncture to fuse together.

12. The apparatus of claim 1 wherein the two electrodes each have an arcuate shape, and the electrodes are spaced opposite of the lumen from each other.

* * * * *